(12) United States Patent
Singh et al.

(10) Patent No.: US 9,908,905 B2
(45) Date of Patent: Mar. 6, 2018

(54) ALUMINUM-MODIFIED POLYSILAZANES FOR POLYMER-DERIVED CERAMIC NANOCOMPOSITES

(71) Applicant: Kansas State University Research Foundation, Manhattan, KS (US)

(72) Inventors: Gurpreet Singh, Manhattan, KS (US); Lamuel David, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 298 days.

(21) Appl. No.: 14/794,322

(22) Filed: Jul. 8, 2015

(65) Prior Publication Data

US 2016/0009741 A1  Jan. 14, 2016

Related U.S. Application Data

(60) Provisional application No. 62/022,000, filed on Jul. 8, 2014.

(51) Int. Cl.

| | |
|---|---|
| *C07F 7/21* | (2006.01) |
| *B82B 1/00* | (2006.01) |
| *H01M 4/38* | (2006.01) |
| *H01M 4/62* | (2006.01) |
| *H01M 4/66* | (2006.01) |
| *H01M 10/052* | (2010.01) |

(52) U.S. Cl.
CPC .................. *C07F 7/21* (2013.01); *B82B 1/00* (2013.01); *H01M 4/386* (2013.01); *H01M 4/62* (2013.01); *H01M 4/625* (2013.01); *H01M 4/661* (2013.01); *H01M 10/052* (2013.01)

(58) Field of Classification Search
CPC  C07F 7/21; B82B 1/00; H01M 4/386; H01M 4/62; H01M 4/625; H01M 4/661; H01M 10/052
USPC ........................................................ 428/446
See application file for complete search history.

(56) References Cited

U.S. PATENT DOCUMENTS 9,453,111 B2 *  9/2016  Singh ............... B82Y 30/00

FOREIGN PATENT DOCUMENTS

WO   WO 2013119806 A1 *  8/2013  ............ B82Y 30/00

OTHER PUBLICATIONS

Bhandavat et al. "Synthesis of Polymer-Derived Ceramic Si(B)CN-Carbon Nanotube Composite by Microwave-Induced Interfacial Polarization", ACS Appl. Mater. Interfaces 2012, 4, 11-16.*
Berger et al. "Solid-State NMR Studies of the Preparation of Si—Al—C—N Ceramics from Aluminum-Modified Polysilazanes and Polysilylcarbodiimides", Chem. Mater, 2004, 16, 919-929.*
Katsuda "Reinforcement of precursor-derived Si—(B-)—C—N ceramics from carbon nanotube", Dissertation, Stuttgart, Germany, 2005.*
Bhandavat et al. "Synthesis, Characterization, and High Temperature Stability of Si(B)CN-Coated Carbon Nanotubes Using a Boron-modified Poly(ureamethyl)Silazane Chemistry", J. Am. Ceram. Soc. 95 [5], 1536-1543 (2012).*
Graczyk-Zajac, M. "Polymer-derived-SiCN ceramic/graphite composite as anode material with enhanced rate capability for lithium ion batteries" Journal of Power Sources, Apr. 5, 2011, vol. 196; pp. 6412-6418.
Graczyk-Zajac, M. "Electrochemical studies of carbon-rich polymer-derived SiCN ceramics as anode materials for lithium-ion batteries," Journal of the European Ceramic Society, Jul. 31, 2010, vol. 30, pp. 3235-3243.
Kaspar, J. "Electrochemical study of lithium insertion into carbon-rich polymer-derived silicon carbonitride ceramics," Electrochimica Acta, Sep. 17, 2010, vol. 56, pp. 174-182.
Su, Dong, "Electrochemical Properties of Polymer-Derived SiCN Materials as the Anode in Lithium Ion Batteries," J. Am. Ceram. Soc., Jul. 1, 2009, vol. 92 (12) pp. 2962-2968.
Kolb, Robert, "SiCN/C-ceramic composite as anode material for lithium ion batteries," Journal of the European Ceramic Society, Mar. 3, 2006, vol. 26, pp. 3903-3908.
Bhandavat, R. "Improved Electrochemical Capacity of Precursor-Derived Si(B)CN-Carbon Nanotube Composite as Li-Ion Battery Anode," Applied Materials & Interfaces, Oct. 2, 2012.

* cited by examiner

*Primary Examiner* — Michael M Bernshteyn
(74) *Attorney, Agent, or Firm* — Hovey Williams LLP

(57) ABSTRACT

Methods for synthesizing aluminum-modified silazanes, their use as polymer-derived ceramic precursors, and polymer-derived ceramics and carbon nanotube core/shell nanocomposites formed therefrom are disclosed.

26 Claims, 13 Drawing Sheets

ALUMINUM-MODIFIED POLYSILAZANES FOR POLYMER-DERIVED CERAMIC NANOCOMPOSITES

CROSS-REFERENCE TO RELATED APPLICATIONS

The present application claims the priority benefit of U.S. Provisional Patent Application Ser. No. 62/022,000, filed Jul. 8, 2014, entitled SYNTHESIS AND EXTREME RATE CAPABILITY OF SIALCN FUNCTIONALIZED CARBON NANOTUBE SPRAY-ON COATINGS AS LI-ION BATTERY ELECTRODE, and incorporated by reference in their entireties herein.

FEDERALLY SPONSORED RESEARCH OR DEVELOPMENT

This invention was made with government support under grant #1335862, awarded by the National Science Foundation. The United States government has certain rights in the invention.

BACKGROUND OF THE INVENTION

Field of the Invention

The present invention relates to polymer-derived ceramics, precursors, and methods of using and making the same.

Description of Related Art

Polymer-derived ceramics, such as silicon carbide (SiC), siliconoxycarbide (SiOC), silicon carbonitride (SiCN), aluminum nitride (AlN), and hafnium carbide (HfC), can be synthesized by thermal decomposition of suitable polymeric precursors, and possess some remarkable properties, such as high oxidation resistance, high temperature piezoresistivity, high mechanical strength, and photoluminescence.

The future success of battery operated vehicles and portable electronic devices will require invention of lightweight, safer, high capacity, long lasting and high power electric sources. From a practical standpoint, advanced lithium ion battery technology (a-LIB) seems to be the most viable option. Therefore, considerable improvements to the present-day LIB electrode and electrolyte materials and design are needed to achieve high rate capability, short charging time, high energy density, and long cycle life. Accordingly, much of the research emphasis has been on the development of high capacity anode materials; particularly silicon anodes because of its high theoretical lithium discharge capacity of 3850 mAh·g$^{-1}$ (>10 times that of commercial graphite). Traditional silicon however has other shortcomings such as low electrical conductivity, large volumetric changes that cause cracking, and unstable solid electrolyte interphase (SEI) formation that leads to poor C-rate and capacity fading. Consequently, several silicon nanostructured electrode design and 3-D assemblies involving shell/core nanowires, nanorods, microspheres and particles etc. have been proposed and fabricated. These new designs have considerably alleviated many of the issues, however, the relatively low volumetric energy densities and challenges associated with their large-scale production and high manufacturing cost must be overcome before such technologies can be commercialized.

SUMMARY OF THE INVENTION

The present invention is broadly concerned with ceramic nanocomposites. The ceramic nanocomposites generally comprise a plurality of carbon nanotubes having respective sidewalls, and a layer of a polymer-derived ceramic adjacent the sidewalls. The polymer-derived ceramic is (non-covalently) bonded to the sidewalls forming a protective shell thereon. The polymer-derived ceramic is formed from an aluminum-modified silazane that is a room temperature liquid-phase polymer. Advantageously, the nanocomposite is resistant to oxidation in flowing air at a temperature of up to about 1000° C. Exemplary nanocomposites include nanowires, nanorods, nanosheets, and combinations thereof.

Articles of manufacture are also disclosed herein, including structures comprising a substrate having a surface and a layer of a polymer-derived ceramic nanocomposite according to the various embodiments of the invention adjacent the substrate surface. Exemplary substrates include metallic surfaces, natural woven fibers, synthetic woven fibers, natural nonwoven fibers, synthetic nonwoven fibers, natural or synthetic mats, natural or synthetic cloth, and combinations thereof. Suitable articles of manufacture include high temperature sensors, turbine blades, engine parts, microelectronic components, solar cells, electrodes, protective coatings, tubing, wires, pump shafts, cylinders, spindles or sleeves, induction coils, and combinations thereof.

The present polymeric precursors and resulting ceramics and nanocomposites have a multitude of uses. Thus, in one or more embodiments, a lithium ion battery electrode is provided, which comprises a nanocomposite according to any one (or combination of) the various embodiments described herein. The lithium ion battery electrode comprises a conductive substrate (e.g., preferably a non-metallic one, like rGO); and a layer of ceramic nanocomposite adjacent the substrate surface. The ceramic nanocomposite comprises a plurality of carbon nanotubes having respective sidewalls; and a layer of a polymer-derived ceramic adjacent the sidewalls, the polymer-derived ceramic being bonded to the sidewalls forming a protective shell thereon, wherein the polymer-derived ceramic is formed from an aluminum-modified silazane that is a room temperature liquid-phase polymer. Preferably, the electrode is an anode for a lithium ion battery. Advantageously, use of the present nanocomposites eliminates the need for separate conducting material (e.g., copper) in the electrode structure. The electrode is preferably substantially free of binder, conductive additives, and current collector metal (e.g., copper).

Protective coatings and molded nanocomposite shapes and structures are also contemplated herein.

The nanocomposites can be provided in various forms, including ceramic coatings, layers, fiber-reinforced composites, and the like. In one or more embodiments, a powdered composition comprising a plurality of free-flowing particulates is described. Each of the particulates consists of a ceramic nanocomposite according to any one (or combination of) the various embodiments described herein. The nanocomposites can be ground into discrete particulates to form a fine powder that is free-flowing and substantially free of solvents. The powder can also be mixed with a solvent system or suitable binder or conducting agent depending upon the final desired use. In some embodiments, the compositions are substantially free of any binders and/or conducting agents. The term "substantially free" as used herein means that the ingredient is not intentionally added or part of the composition, although it is recognized that residual or incidental amounts or impurities may be present in low amounts (e.g., less than about 0.5% by weight, based upon the total weight of the composite taken as 100% by weight).

Also described herein are methods of forming polymer-derived ceramic nanocomposites. The methods generally comprise mixing a plurality of carbon nanotubes with an aluminum-modified silazane that is a room temperature liquid-phase polymer to yield respective sidewall-functionalized nanotubes comprising a layer of aluminum-modified silazane adjacent the nanotube sidewall. The layer of aluminum-modified silazane is crosslinked to yield a pre-ceramic nanocomposite comprising a solid pre-ceramic layer adjacent the sidewall of the carbon nanotubes. The pre-ceramic layer comprises a crosslinked network of aluminum-modified silicon-based compounds coating the sidewall of the nanotubes. The pre-ceramic layer is then converted to ceramic to yield a ceramic nanocomposite comprising a layer of aluminum-modified polymer-derived ceramic coating the sidewall of the nanotubes.

Methods of forming a polymer-derived ceramic coating are also disclosed. The methods generally comprise dispersing a ceramic nanocomposite powder in a solvent system to form a ceramic dispersion. The powder comprises discrete particulates, each of the particulates comprising a nanocomposite according to any one (or combination of) the various embodiments described herein. The ceramic dispersion is then applied to a substrate surface to form a layer thereon. The layer is heated to evaporate the solvent system and yield a coated substrate having the ceramic nanocomposite coating adjacent the substrate surface.

Also described here are pre-ceramic nanocomposites. The pre-ceramic nanocomposites comprise a plurality of carbon nanotubes having respective sidewalls, and a pre-ceramic layer adjacent the sidewalls. The pre-ceramic layer comprises a crosslinked network of aluminum-modified silicon-based ceramic precursor compounds bonded to the sidewalls.

Regardless of the embodiment, the aluminum-modified silazanes and resulting ceramic nanocomposites have a number of significantly improved properties over existing precursors and polymer-derived ceramics, as explained in more detail below.

DETAILED DESCRIPTION OF PREFERRED EMBODIMENTS

Figure 1:
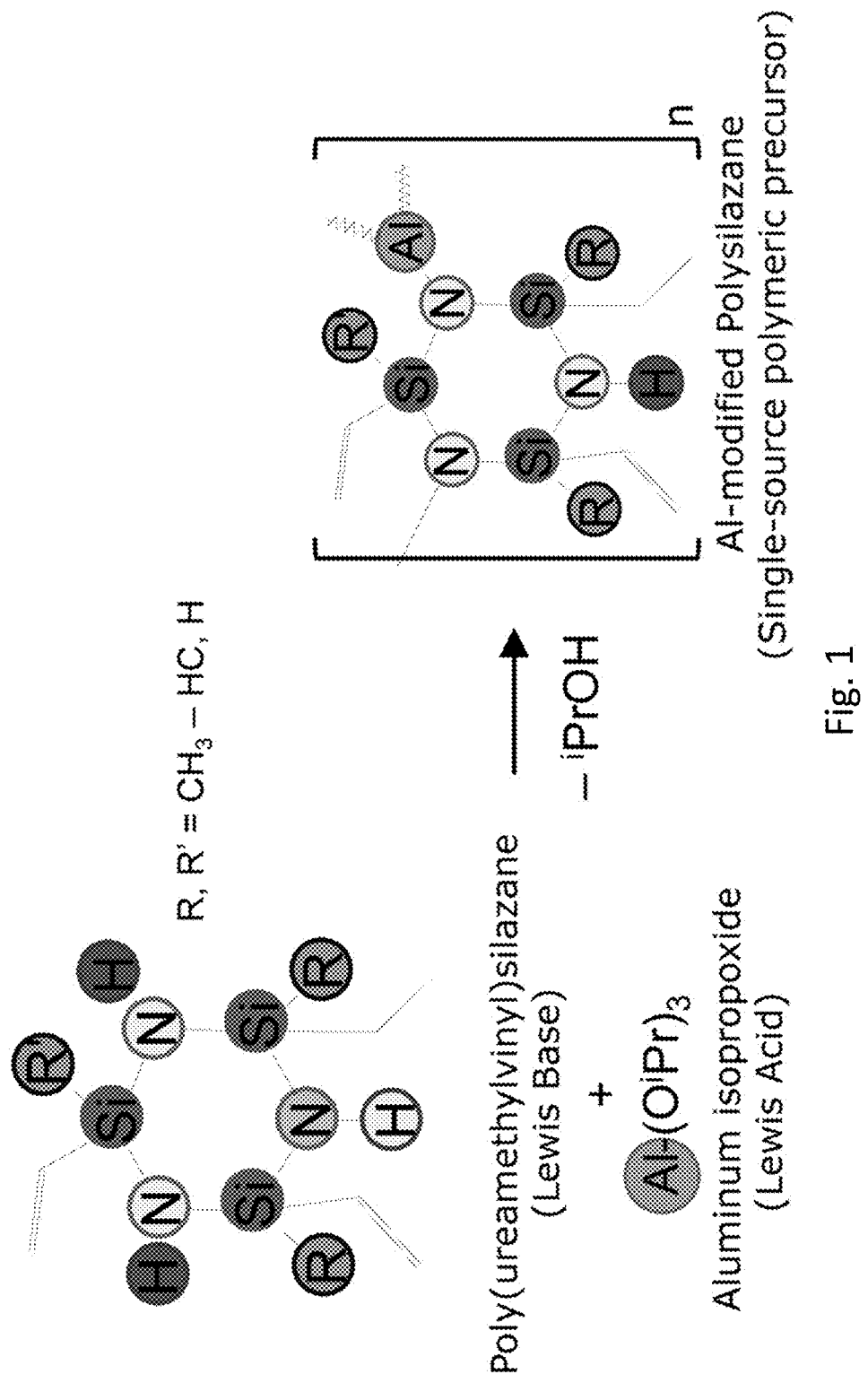
FIG. 1 shows the reaction mechanism for molecular level interfacing of poly(ureamethylvinyl)silazane liquid polysilazane with aluminum.

In one or more embodiments, the present invention is concerned with aluminum-modified silazanes ("polyaluminasilazanes"), their use as polymer-derived ceramic precursors, and polymer-derived ceramics and composites formed therefrom. The methods comprise mixing a room temperature liquid-phase, non-oxide silicon-based ceramic precursor compound with an aluminum alkoxide (e.g., isopropoxide) for at least about 12 hours (preferably from about 12 to about 24 hours, with continual mixing) under ambient conditions. The term "ambient conditions," as used herein refers to the common, prevailing, and uncontrolled conditions in a room or place, such as room temperature (about 20-35° C.) and normal atmosphere and pressure (about 1 atm), and without artificial constraints. In other words, aluminum-doping reactions according to the invention do not have to be carried out under any elevated temperatures or pressures, or in an otherwise artificial environment (e.g., under vacuum, under Ar or $N_2$ gas, etc.). In some embodiments, the reaction mixture may be heated during mixing to temperatures of from about 25° C. to about 85° C. to facilitate drying of any solvent (if present, see infra), as well as evaporation of any by-products, although the reaction otherwise proceeds under ambient conditions. In some embodiments, sonication can be used to facilitate intermixing of the ingredients to create a substantially homogeneous reaction mixture.

Preferably, the non-oxide silicon-based compound is a silazane compound of the oligomer/polymer-type, referred to herein generally as a "polysilazane." Polysilazanes are room temperature liquid-phase polymers of low viscosity, where the term "polymer" is used herein to encompass both oligomers and polymers. The term "room temperature liquid-phase" as used herein, means that the polymer is a flowable, liquid-phase material, without the aid of solvents or heating to soften the material and lower its viscosity. Thus, such materials are in the liquid-phase (as opposed to the gel, semi-solid, or soft-solid phases) at or about room temperature (e.g., from about 20 to about 35° C.), and in any event at temperatures below 50° C. Thus, in some literature, such polymers are described as 100% "solids" polymers (i.e., not dispersed in a solvent) in the liquid phase, which can be solidified (cured) under appropriate conditions upon heating to sufficient temperatures. Suitable silazanes for use in the various embodiments include any type of polysilazane, including functional derivatives thereof. For example, many commercially-available polysilazanes include functional groups, such as methyls, vinyls, aryls, alkyls, allyls, amines, phenyls, and the like, pendant from the backbone to improve stability of the polymer and/or facilitate crosslinking/curing. Exemplary polysilazanes will generally comprise (consist essentially, or even consist of) monomeric repeat units comprising (consisting essentially or even consisting of) alternating silicon and nitrogen atoms in the polymer backbone. In one or more embodiments, the monomeric repeat units comprise (consist essentially or even consist of) alternating silicon and nitrogen, generally of the formula:

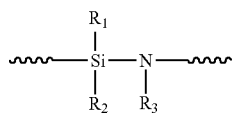

where each of $R_1$ and $R_2$ are individually —H, alkyls (e.g., $C_1$-$C_4$ alkyls), alkenyls (e.g., vinyl groups, etc.), or alkynls (e.g., —C≡CH), and $R_3$ is —H, alkyl, aryl, or allyl. The foregoing segment may correspond to one monomeric repeat unit in the polymer backbone, but may also represent a portion of the backbone smaller than an entire repeat unit where additional atoms are attached to either the nitrogen or the silicon within the repeat unit, as indicated by the squiggly lines. Thus, the squiggly line indicates the point of attachment to the remainder of the backbone or molecule. The foregoing segment may also represent a repeat segment of a cyclic polymer, with repeating Si—N units forming the ring, as illustrated below:

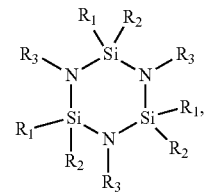

where $R_1$, $R_2$, and $R_3$ are defined above.

In some embodiments, additional atoms, such as alternating carbons, can be present in the backbone of the Si—N repeat unit ("organopolysilazanes" or "polycarbosilazanes"), or in adjacent repeat units. Thus, in one or more embodiments, the monomeric repeat units will comprise (consist essentially or even consist of) the general formula:

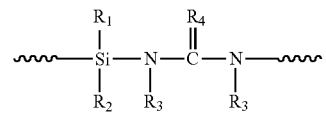

where $R_1$, $R_2$, and $R_3$ are defined above, and $R_4$ is O or S. In one or more embodiments, at least one of $R_3$ is —H. Thus, in some embodiments, suitable polysilazanes will comprise (consist essentially or even consist of) monomeric repeat units of:

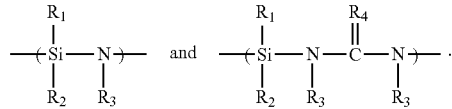

Polysilazanes are commercially-available (e.g., Ceraset™ from KiON, Clariant, etc.), and can also be synthesized using numerous known techniques. Various polysilazane synthesis routes are described, for example, in U.S. Pat. No. 5,021,533 and U.S. Pat. No. 5,190,709, incorporated by reference herein to the extent not inconsistent with the present disclosure.

Regardless of the embodiment, a reaction mixture of polysilazane and aluminum isopropoxide is formed. The relative amounts of polysilazane to aluminum isopropoxide in the mixture is tunable, and can be varied depending upon the final properties desired in the polymeric precursor composition. In general, the weight ratio of polysilazane to aluminum isopropoxide will range from about 2:3 to about 9:1, preferably from about 7:3 to about 4:1, more preferably from about 3:2 to about 2:1, and even more preferably about 13:7.

In one or more embodiments, the reaction mixture comprises, consists essentially, or even consists of the polysilazane and aluminum isopropoxide. In some embodiments, solvents may be present in the reaction mixture such as toluene, propanol, N-methyl pyrrolidone, and the like. In some embodiments, the reaction mixture is substantially free (preferably less than about 0.5% by weight) of any additives or additional ingredients, such as solvents, reaction salts, and the like. Reaction of the polysilazane with the aluminum isopropoxide results in an incorporation (substitution) of aluminum atoms into the polysilazane structure at the molecular level (and not just as fillers) to yield an aluminum-modified silazane (aka "polyaluminasilazane") liquid ceramic precursor composition. Thus, the aluminum-modified ceramic precursor liquid composition comprises, consists essentially, and preferably consists of the aluminum-modified silazane.

Advantageously, aluminum-modified silazanes formed according to the present invention remain in liquid phase under ambient conditions without a solvent system. That is, they do not gel or harden into self-sustaining, semi-solid, or soft-solid phases at room temperature, where the term "self-sustaining" means that the gel or semi-solid is not susceptible to deformation merely due to its own internal forces, and substantially maintains its shape without an external support structure. Thus, the aluminum-modified silazanes according to embodiments of the invention remain flowable polymer liquids under ambient conditions and are particularly suited for injection molding, liquid casting, fiber drawing, melt spinning, and/or infiltration/impregnation techniques. For example, the liquid ceramic precursor composition can be poured, spin coated, spray coated, injected, puddle, pressed, and the like (without first being dispersed in a solvent system), which provides significant advantages over the state of the art. In one or more embodiments, the aluminum-modified silazanes according to the invention will have a viscosity of less than about 210 cP at 25° C.

In one or more embodiments, the aluminum-modified silazanes will comprise (consist essentially or even consist of) recurring monomeric units comprising aluminum-nitrogen bonds (and silicon-nitrogen bonds). In some embodiments, the monomeric units can further comprise aluminum-oxygen bonds. Aluminum doping results predominantly in aluminum-nitrogen bond formation, and little if any aluminum-carbon bond formation. In some embodiments, the aluminum-modified silazanes will comprise aluminum substitutions off of nitrogen atoms in the polymer backbone, but can alternatively comprise aluminum-substituted nitrogen groups pendant from the silicon atoms in the polymer backbone. In any event, after incorporation of aluminum into the polymer at the molecular level, the monomeric units will comprise —Si—N—Al(R$_5$)$_2$ bonds, where each of R$_5$ is —O—CH$_2$—CH$_2$—CH$_3$. In one or more embodiments, the recurring monomeric units in the resulting aluminum-modified silazanes will comprise alternating silicon and aluminum-substituted nitrogen atoms of the formula:

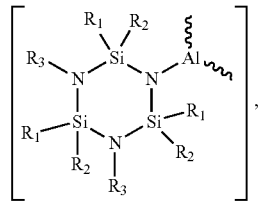

where R$_1$, R$_2$, and R$_3$ are defined above, and the squiggly lines preferably represent R$_5$ (defined above).

The aluminum-modified silazanes can be converted into SiAlCN ceramics having substantially improved properties, such as oxidation resistance, extremely high temperature resistance, chemical and structural stability, and the like. A particular advantage of the present aluminum-doped ceramic precursors is that they can interface with nanomaterials to create nanocomposites. The term "nanocomposite," as used herein refers to combinations of the ceramics with nanomaterials that involve surface wetting and functionalization of the nanomaterial by the liquid polymeric precursors resulting in a chemical interfacing between the ceramic and the nanomaterial. More particularly, the aluminum-modified ceramic precursor can be used to create a functionalized layer on the nanomaterial surfaces.

Exemplary nanomaterials include carbon nanotubes. Carbon nanotubes (CNTs) are allotropes of carbon (fullerene molecules) characterized by cylindrically-shaped graphene side walls. Carbon nanotubes have a substantially hollow cylindrical shape defined by a nanotube sidewall. The nanotube sidewall has exterior and interior cylindrical surfaces, and extends along a length between two terminal ends. Although it will be appreciated that carbon nanotubes do not always have a perfectly circular cross-sectional shape, carbon nanotubes are generally considered to have a "diameter" (i.e., maximum surface-to-surface dimension as measured from the external cylindrical surface bisecting the tube in a direction perpendicular to the length). Carbon nanotubes can be categorized as single-walled carbon nanotubes (SWNTs), double-walled carbon nanotubes (DWNTs), and/or multi-walled carbon nanotubes (MWNTs). SWNTs consist of a single rolled layer of graphene, whereas MWNTs consist of multiple rolled layers (concentric tubes) of graphene. The size of the carbon nanotubes can vary widely, with the average (mean) diameter of SWNTs being from about 0.5 to about 5 nm. Carbon nanotubes are extremely strong and light, possess high microwave absorbance characteristics, and can act both as conductors or semiconductors depending on the diameter and chirality of the hexagonal carbon sidewall lattice along the length of the nanotube.

The aluminum-modified ceramic precursor liquid composition is mixed with the carbon nanotubes to form a ceramic composite precursor composition. Preferably, the carbon nanotubes are first dispersed in a solvent system, followed by mixing with the ceramic precursor. Any suitable solvent system can be used in which carbon nanotubes can be dispersed and which is miscible ("compatible") with the ceramic precursor polymer. Regardless, the carbon nanotubes and ceramic precursor are preferably mixed for a time period of from about 8 to about 48 hours (and preferably from about 12 to about 24 hours), under ambient conditions. The resulting mixture is then dried (to drive off solvents) under artificial conditions, and preferably under inert (N$_2$) atmosphere at elevated temperatures of from about 70 to about 100° C., for a time period of from about 12 to about 24 hours (or until all solvent has evaporated). In one or more embodiments, the resulting ceramic composite precursor comprises (consists essentially or even consists of) the aluminum-modified ceramic precursor liquid composition and a plurality of carbon nanotubes distributed therein. The amount of carbon nanotubes used in the ceramic composite precursor composition can be varied, but will typically range from about 5 to about 20% by weight, and preferably from about 5 to about 10% by weight, based upon the total weight of the precursor composition taken as 100% by weight. The resulting solvent-less ceramic composite precursor comprises (and preferably consists essentially or even consists of) carbon nanotubes with their sidewall surfaces (preferably exterior sidewall surface) functionalized with aluminum-modified ceramic precursor polymer.

The aluminum-modified silazane ceramic precursor coating can then be solidified through crosslinking to yield pre-ceramic nanocomposites. In particular, the functionalized carbon nanotubes can be heated to a temperature of from about 700 to about 1500° C. (preferably from about 900 to about 1100° C.) for about 2 to about 12 hours (preferably from about 4 to about 6 hours) at a rate of from about 2 to about 10° C./min. (preferably about 5° C./min.).

Crosslinking can take place under artificial atmosphere (e.g., $N_2$ or $NH_3$) if desired. Crosslinking transforms the aluminum-modified silazane ceramic precursor coating into a solid pre-ceramic layer adjacent the sidewall of the carbon nanotubes. The resulting pre-ceramic nanocomposites make up a dry particulate composition, wherein the individual particulates each comprise (consists essentially, or even consists of) a crosslinked network of aluminum-modified silicon-based compounds coating the sidewall of the nanotubes. The crosslinked network is characterized by aluminum crosslinks (Al-enriched string-like regions) linking the silicon-based compounds (Al-poor regions).

The pre-ceramic composite can then be pyrolyzed. In one or more embodiments, the pre-ceramic composite can first be converted into a free-flowing powder (e.g., by grinding, milling, pulverizing, or otherwise crushing the pre-ceramic composition), followed by pyrolysis. As used herein, the term "free-flowing" means that the individual particulates remain loose with the ability to readily flow in response to shear forces, and do not have a tendency to cake or lump together into agglomerates.

Ceramic formation requires heating the pre-ceramic composite up to at least about 700° C., and preferably at least about 1,000° C., for at least about 2 hours (preferably from about 4 hours to about 12 hours), at a rate of from about 2 to about 10° C./min. (preferably about 5° C./min.) to yield the ceramic nanocomposite. Pyrolysis can take place under artificial atmosphere (e.g., $N_2$ or $NH_3$) if desired. It will be appreciated that the pyrolysis temperature can be varied depending upon the final desired properties of the ceramic coating. For most ceramic applications, the pre-ceramic composite can be heated to temperatures of between about 800° C. and 1100° C. for pyrolysis. For use as electrodes (anodes) in lithium ion batteries, temperatures between about 800° C. and 1000° C. are preferred. If a lower oxygen content in the final ceramic is desired, the precursor can be heated up to about 1500° C.

The resulting ceramic composite is a free-flowing (dry) black powder, wherein the individual particulates comprise (consist essentially or even consist of) carbon nanotubes having their sidewall surfaces (e.g., exterior) functionalized by a layer of aluminum-modified polymer derived ceramic. The aluminum-modified polymer-derived ceramic layer is characterized by aluminum substantially uniformly distributed throughout the polymer-derived ceramic network (e.g., Si—N moieties and compounds, such as Si—N rings).

Thus, the inventive nanocomposites in one or more embodiments, will comprise an aluminum-modified silazane-derived ceramic shell adjacent the carbon nanotube sidewall surface. Such nanocomposites can be characterized as a carbon nanotube core/polymer-derived ceramic shell nanowires, nanorodes, or nanosheets. As noted previously, the aluminum-modified polymer-derived ceramic is not merely a ceramic matrix (continuous phase) or coating in which the carbon nanotubes are physically distributed (dispersed phase). Rather, the aluminum-modified polymer-derived ceramic shell has chemically interfaced with and bonded (non-covalently) to the carbon nanotube sidewall surface, resulting in a significantly stronger composite structure. Moreover, the composites have significantly improved oxidation resistance of up to about 1000° C. in air.

Nanocomposites according to the invention can be converted to ceramic using conventional heating (e.g., furnace); however, microwave irradiation can also be used to generate heat in the composite sufficient for thermal decomposition of the polymeric precursor into the ceramic phase. Remarkably, the conversion to ceramic using microwave irradiation takes less than about 30 minutes, preferably less than about 20 minutes, and more preferably from about 5 to about 20 minutes.

Regardless of the embodiment, the composites or nanocomposites can be used as formed, such as by molding the liquid ceramic composite precursor into the desired shape before crosslinking and/or pyrolysis. Likewise, dispersions can be created by dispersing the dried ceramic composite precursor particulates in a solvent system, dispersing the pre-ceramic composite particulates in a solvent system, or dispersing the ceramic composite particulates in a solvent system, followed by forming a coating (and crosslinking and/or pyrolysis, as needed). Similarly, the pre-ceramic composite and/or ceramic composite can be ground into a free-flowing powder and used to form a coating (followed by pyrolysis if applicable). Coatings of powdered nanocomposites can be formed using conventional powder-coating techniques. The powder can also be dispersed in a suitable solvent system, or combined with suitable binders to facilitate coating formation. The powdered nanocomposites can be applied to virtually any type of substrate. Moreover, it will be appreciated that the powder itself can be used as a filler for a further composite material. Exemplary uses of the powdered boron-modified polymer-derived ceramic include coatings (e.g., turbine blades, engine parts), matrix composites, surface tiles, industrial use components, and the like.

The fact that the ceramic composite precursor composition mixture is in the liquid phase expands the potential uses for these improved materials. For example, the ceramic composite precursor composition can be applied to a substrate surface, such as by spray coating or spin coating, followed by crosslinking and eventual pyrolysis to form a ceramic coating or film on the substrate surface. More preferably, the liquid ceramic composite precursor composition mixture can be cast or molded into the desired shape, followed by crosslinking and pyrolysis into ceramic. Thus, ceramic bricks or tiles could be made. Likewise, various-shaped ceramic parts can be fabricated as desired.

Similarly, the ceramic composite powder can also be used to create improved ceramic coatings. As noted above, the ceramic composite powder can be dispersed in a solvent system. In general, suitable solvent systems will include a solvent selected from the group consisting of alcohols (e.g., isopropanol), toluene, other organic solvents, and mixtures thereof. This ceramic dispersion can then be applied to a substrate surface, such as by spraying, puddling, spin coating, brushing, or the like. The coating can then be heated to drive off solvents and "set" the coating. Thus, the heating temperature will depend upon the boiling point of the particular solvent system used. In general, the layer can be heated to temperatures ranging from about 60 to about 100° C., for time periods of from about 30 to about 1440 min. The process yields an improved ceramic composite coating adjacent the substrate surface. The coating can be laid down in various thicknesses, as desired. In general, the amount of ceramic composite particles present in the dispersion will be at least about 5% by weight, and preferably from about 10 to about 20% by weight, based upon the total weight of the dispersion taken as 100% by weight.

The ceramic composite also has high optical absorbance characteristics, making it ideal for applications involving optical absorbance (e.g., solar cells). The ceramic composite layer is also resistant to laser irradiation, which makes it ideal for use in laser welding. It has been shown to absorb laser light without damage, and when applied to a metal substrate, can be used to direct heat to the metal substrate for welding. The term "resistant to damage" means that the ceramic will not burn, delaminate, or deform. For example, the ceramic composite layer is resistant to laser irradiation up to about 8 kWcm$^{-2}$ at a wavelength of about 1 μm at 10 kW average power, for about 10 seconds without burning, delamination, or deformation of the layer.

Moreover, it will be appreciated that the powder itself can be used as a filler for a further composite material.

The liquid compositions and composite powders described herein can be applied to virtually any type of substrate including planar substrates as well as those having rough or intricate non-planar geometries (e.g., curved surfaces). Suitable substrates include metallic and non-metallic surfaces, such as those found in engine parts, tubing, wires, pump shafts, cylinders, spindles and/or sleeves, induction coils, natural and/or synthetic woven and/or nonwoven fibers, mats and/or cloth, and the like. Such techniques would be useful for the formation of various articles of manufacture, such as harsh environmental or high temperature sensors, turbine blades, microelectronic components, solar cells, electrodes, protective coatings, and the like. Exemplary metallic substrates include copper and alloys thereof.

For example, in one or more embodiments, a mat, such as a carbon nanotube mat or cellulose mat substrate can be formed by filtering a dispersion of the carbon nanotube or cellulose through a filter containing filter paper of the appropriate size, which results in deposition of the material onto the filter paper in a nonwoven mat. The mat can be peeled away from the filter and separated from the filter paper to yield a freestanding mat, network, or sheet. The ceramic or preceramic powder can be applied to the mat, followed by pyrolysis and/or drying as necessary. This technique can be used to yield a thin ceramic film adjacent the carbon nanotube or cellulose mat. This ceramic "paper" composite is thin and flexible with a uniform paper surface, which has a much higher temperature stability than the uncoated mat. Such ceramic coated paper composites be used as an independent anode material in rechargeable lithium-ion batteries. The inventive composite simplifies the anode design by eliminating the binder, conductive additives, and current collector metal (e.g., copper). The robust SiAlCN/CNT shell/core composite offers extreme C-rate capability as a battery electrode. Addition of Al to the molecular network of SiCN alone improves electrical conductivity of SiCN by three orders of magnitude, while interfacing with CNTs showed even higher conductivity reaching approximately 0.2 S cm$^{-1}$. The Si—Al—C—N/CNT electrode showed stable charge capacity of 577 mAh g$^{-1}$ at 100 mA g$^{-1}$ and a remarkable 400 mAh g$^{-1}$ at 10,000 mA g$^{-1}$, which is the highest reported value for a silazane derived glass-ceramic or nanocomposite electrode. Under symmetric cycling conditions, a high charge capacity of ~350 mA g$^{-1}$ at 1600 mA g$^{-1}$ was continuously observed for over 1000 cycles.

Further, it will be appreciated that the spray-coating technique for nanocomposite electrode preparation eliminates polymeric binder and conductive agent thereby reducing processing steps and eradicating foreign material in the electrode. That is, in traditional cells, where the electrode is prepared by slurry coating a mixture of active material with conducting agent (generally carbon black) and polymeric binders in 8:1:1 ratio, our anode is prepared by spray coating of the as-prepared composite dispersions directly onto the metal current collector foil.

Carbon nanotube paper has also been used to fabricate flexible actuators, sensors, displays, and energy storage devices, which can be further enhanced by addition of the inventive ceramic film.

The aluminum-modified ceramic nanocomposite can also be used to prepare flame-resistant protective gear and clothing. Thus, a coating of the aluminum-modified ceramic or preceramic nanocomposites can be formed on a cloth substrate, by dipping, spray-coating, etc., followed by drying and/or conversion of to a ceramic as necessary.

Polymer-derived ceramics and associated nanocomposites not only have high temperature oxidation resistance, but are also resistant to laser irradiation. Thus, ceramics and associated nanocomposites according to any one (or combination) of embodiments described herein are resistant to damage when irradiated with a laser up to about 15 kWcm$^{-2}$ at a wavelength of about 10.6 μm for about 10 seconds. The term "resistant to damage" means that the ceramic will not burn, delaminate, or deform. The ceramics and associated nanocomposites also have uniform absorbance, and more specifically high optical absorbance characteristics. Thus, at wavelengths of about 10.6 μm, the ceramics and/or nanocomposites will absorb at least about 90%, preferably at least about 95%, and more preferably at least about 98% of radiation.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Materials and Instrumentation

Aluminum propoxide (99.9% Sigma Aldrich) and poly(ureamethylvinyl)silazane (Ceraset™; Clariant Corporation) were used as received without further purification.

Scanning electron microscopy (SEM) of the synthesized material was carried out on Carl Zeiss EVO MA10 system with incident voltage of 5 KV to 30 KV. TEM images were digitally acquired by use of a Phillips CM100 and FEI Tecnai F20 XT operated at 100 KV. SS-NMR Experiments were carried out on a Bruker Avance II 300 spectrometer (Billerica, Mass.) operating at a static magnetic field of 7.05 T. Samples were packed into 4 mm zirconia rotors. The magic angle spinning speed was 12 kilohertz, the spectral width was 50,000 Hz, the pulse delay 1 second, and a direct excitation pulse of 0.6 microseconds was used. The surface chemical composition was studied by X-ray photoelectron spectroscopy (XPS, PHI Quantera SXM) using monochromatic Al Kα X-radiation.

Preparation of SiAlCN/CNT Composite

The "as-obtained" 1 g of CNTs (Arkema™) were dispersed in 1 g $L^{-1}$ sodium dodecyl benzene sulfonate (NaDDBS) (Sigma Aldrich) aqueous solution, followed by sonication for 1 h to remove any unwanted agglomerations. The dispersed nanotubes were then washed repeatedly with DI water to eliminate any excess NaDDBS or related impurities, followed by slow drying that yielded a dry CNT mass. These dried nanotubes (approx. 1 g) were then dispersed in toluene (125 mL) for further functionalization.

The Al-modified polymeric ceramic precursor was prepared by adding aluminum propoxide to the room-temperature, liquid polysilazane in 10:90 weight ratio followed by physical mixing at room temperature for 24 hours to yield aluminum-functionalized polysilazane precursor compounds.

The Al-modified ceramic precursor was then slowly added and stirred into 5 wt % CNTs dispersed in toluene. After the mixture was stirred for approx. 24 h, it was dried in inert atmosphere at 80° C. The dried mixture was then transferred to a tube furnace where it was heated to 300° C. for approximately 4 hours for crosslinking of the ceramic precursor, followed by a pyrolysis at 1000° C. for 5 hours in nitrogen atmosphere at 5° C. $min^{-1}$ heating and cooling rates to yield a SiAlCN/CNT composite.

A SiAlCN powder specimen was prepared in a similar manner as described above. Briefly, the prepared liquid Al-modified polymeric precursor was first cross-linked in a vertical tube furnace at approx. 300° C. in $N_2$ for 4 hours resulting in an infusible mass, which was then ball milled for 2 hours and pyrolyzed at 1000° C. for 5 hours in $N_2$ resulting in a fine black SiAlCN powder. The polymer to ceramic yield was approx. 60 to 70%.

Anode Preparation

The SiAlCN/CNT composite material was gently crushed using a mortar-pestle to obtain a fine powder (approx. 1 to 2 µm in size, as determined by the SEM). The powder was then dispersed in a toluene/NMP mixture (1:1 by weight) (ACS reagent) and sonicated for 1 hours to obtain uniform dispersions. After keeping the dispersion stable for 12 hours, the solution at the top was decanted (concentration observed to be ~8 mg·$mL^{-1}$) and later carefully sprayed on heated copper foil by use of an airbrush at 15-psi air pressure. The spraying was done with passes (with a single pass lasting for approx. 5 seconds followed by 10 seconds of break) while the substrate surface temperature was raised to about 180° C. Frequent stops between the passes allowed the solvent to evaporate and thereby form a uniform compact coating. Spray coating was carried out until the appropriate dark black coating thickness was visually realized. The coated copper foils were then maintained at 150° C. on a hot plate for about 12 hours to ensure removal of volatile components. The material loading varied from about 0.12 to 0.2 mg $cm^{-2}$. 'Neat' SiCN, SiAlCN particles, and MWCNT electrodes were also prepared in a similar manner without using conducting agents or binders. However, SiCN and SiAlCN dispersions were not stable and the coating adhesion to the copper foil was generally poor.

Coin-Cell Assembly

Half-cell batteries were made by punching 14.3-mm diameter circles out of the foil for use as working electrode. A few drops of electrolyte solution of 1M $LiPF_6$ (Alfa Aesar) dissolved in (1:1 v/v) dimethyl carbonate: ethylene carbonate (ionic conductivity 10.7 mS $cm^{-1}$) was used. A glass separator, soaked in electrolyte was placed between the working electrode and pure lithium metal (14.3 mm diameter), which acted as counter electrode. Washer, spring and a top casing were placed on top to complete the assembly before crimping. The whole procedure was carried out in an Ar-filled glovebox. Electrochemical performance of the assembled coin cells was tested using a multichannel BT2000 Arbin test unit sweeping between 2.5 V to 10 mV vs Li/$Li^+$ using following cycle schedule: (a) Asymmetric mode: Li was inserted at 0.1 A $g^{-1}$ (w.r.t. weight of the coating), while the extraction was performed at increasing current densities of 0.1, 0.2, 0.4, 0.8, 1.6, 3.2, 6.4 and 10 A $g^{-1}$ for 5 cycles each, and returning back to 0.1 A $g^{-1}$ for the next 10 cycles. (b) Symmetric mode: Later, all the cells were subjected to symmetric cycling at a current density of 1.6 A $g^{-1}$ for up to 1000 cycles, returning back to 0.1 A $g^{-1}$ for the last 100 cycles.

Results and Discussions

Synthesis and Characterization

FIG. 1 illustrates the proposed reaction mechanism for Al-doping of poly(ureamethylvinyl)silazane. The addition of aluminum propoxide to polysilazane results in formation of covalent bond between the electron pair donor nitrogen and electron deficient aluminum. Due to steric hindrance it is assumed that aluminum propoxide can undergo reaction with polysilazane at few N—H bonds forming aluminum containing chainlike structures. The schematic in FIG. 2 describes the overall approach toward synthesis of SiAlCN/CNT ceramic composite and its subsequent spray coating method for electrode preparation. Functionalization of CNTs is expected to involve non-covalent bonding of as-synthesized liquid Al-modified polysilazane with the surfaces of CNTs. During cross-linking step at 300° C., the propoxy ion from aluminum propoxide combines with weakly bonded hydrogen in Si—N polymer backbone, thereby releasing propanol as a byproduct. This thermal cross-linking leads to a 3-D network where aluminum is preferentially enriched in string like regions separated by aluminum-poor regions. On further pyrolysis at 1000° C., reaction of aluminum alkoxide with Si—H and N—H bonds facilitates distribution of aluminum in flexible chainlike blocks along with large Si—N rings throughout the matrix.

Figure 2:
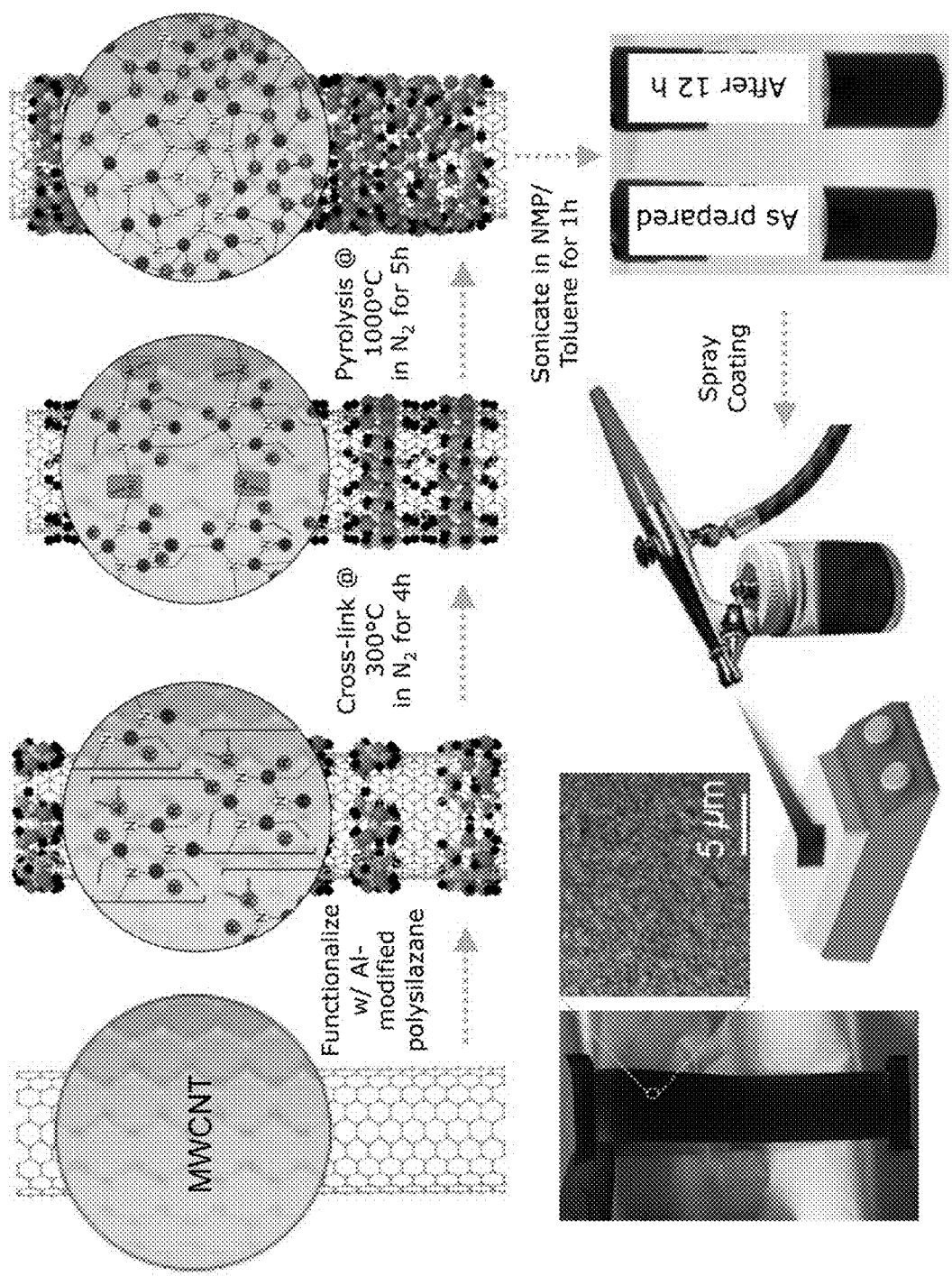
FIG. 2 shows a schematic of the overall approach toward synthesis of SiAlCN/CNTs nanocomposites and electrode preparation by spray-coating technique. (L to R): Al doped polymeric precursor wets the CNTs surface forming a uniform layer. During heating in flowing $N_2$, the polymer first cross-links at 300° C. forming 3-D network where Al is preferentially enriched in string-like regions separated by Al-poor regions. Later, during pyrolysis the reaction of aluminum alkoxide with Si—H and N—H bonds facilitates homogeneous distribution of aluminum in flexible chainlike blocks along with large Si—N rings throughout the matrix. The as-obtained ceramic/CNT is then sonicated in toluene/NMP mix to form a stable dispersion, which is then spray coated onto a copper foil (approx. 6"×2") kept on a hot plate.
Figure 3:
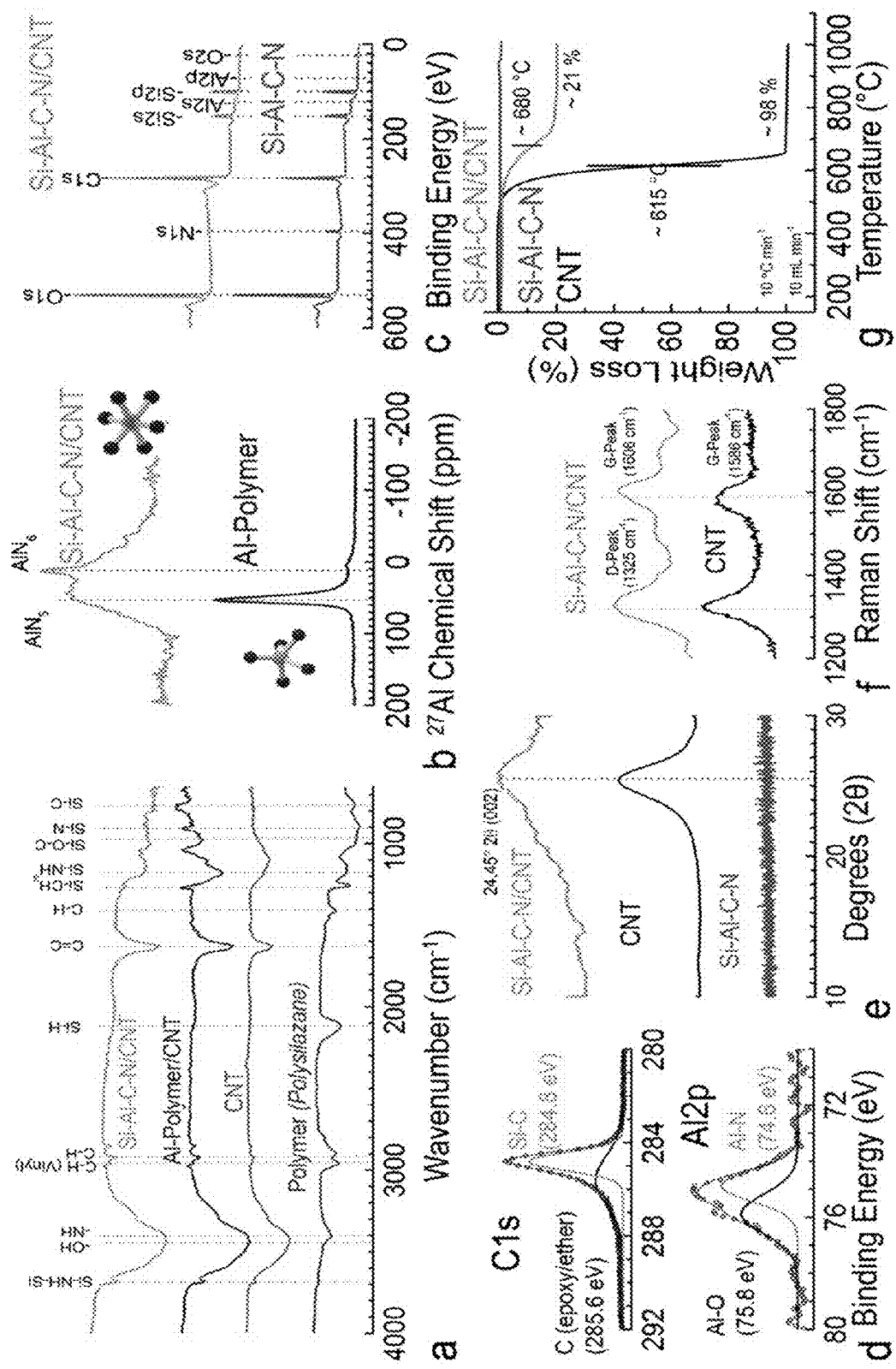
FIG. 3 shows data for (a) FTIR comparison of SiAlCN/CNTs (before and after pyrolysis) and CNTs along with the as-obtained polysilazane precursor. (b) 27Al NMR spectra of SiAlCN/CNT and Al modified polysilazane polymer. (c) X-ray photoelectron spectroscopy plot of SiAlCN and SiAlCN/CNTs. Peak characteristic to Al2s and Al2p could be observed in both the specimens. (d) High-resolution XPS of SiAlCN/CNTs composite showing the characteristic C1s and Al2p peaks. (e) XRD data confirming the amorphous structure of SiAlCN and presence of CNTs in SiAlCN/CNTs. (f) Comparison of Raman spectra of CNTs and SiAlCN/CNTs. The characteristic D-peak and G-peaks are clearly observed. (g) Thermogravimetric analysis plot of CNTs and SiAlCN/CNT hybrid composite.

A range of spectroscopic analyses was performed to confirm the presence of Al in the polymer, its cross-linking behavior, and the functionalization of CNTs with SiAlCN ceramic as proposed in FIG. 2. We compared the FTIR spectra of SiAlCN/CNT with its cross-linked polymer counterparts and 'neat' CNTs (FIG. 3a). The small peak at 3680 cm$^{-1}$ and a broad peak between 3480 and 3400 cm$^{-1}$ are characterized to free and bonded —OH stretching, most likely due to moisture absorption. The FTIR spectrum of polysilazane is similar to what has been previously reported in the literature. The peaks ascribed to vinyl groups are the C—H vibrations at 2950 cm$^{-1}$. The peak attributed to Si—NH—Si group is Si—N vibration at 1160 cm$^{-1}$. Si—CH$_3$ characteristic peak was observed at 1253 cm$^{-1}$ and methyl vibrations at 2954 and 2910 cm$^{-1}$. The large peak at 2111 cm$^{-1}$ is attributed to Si—H. The broad band between 640 and 1000 cm$^{-1}$ is resultant to merger of two bonds: Si—C and Si—N. The major noticeable difference in the SiAlCN/CNT spectra is the peak at 1620 cm$^{-1}$ which corresponds to C=C bond. Further, the Si—CH$_3$ groups (1253, 2954 and 2896 cm$^{-1}$) and Si—H peak at 2114 cm$^{-1}$ could not be prominently observed due to elimination of H$_2$ and methyl groups during pyrolysis. The peaks that cover Si—C, Si—N, Al—N and C—C at the lower wavenumber range (<1400 cm$^{-1}$) suggest mixture of bonds. Further characterization of the composite was carried out using solid-state NMR ($^{27}$Al). FIG. 3b compares the $^{27}$Al NMR spectra of SiAlCN/CNT before and after pyrolysis. The spectra obtained before pyrolysis shows one distinct peak at 51 ppm, corresponding to AlN$_5$ structures. While after pyrolysis a new peak centered at 8 ppm corresponding to AlN$_6$ evolved along with AlN$_5$. These results suggest the presence of both pentavalent and hexavalent Al but no 4-fold coordinated aluminum nuclei (generally observed at 100 ppm) could be characterized in the ceramic structure. Based on the FTIR and NMR analysis, we can confirm the broad structure of the amorphous ceramic shell deduced in FIG. 2. Additional analysis involved XPS of the SiAlCN/CNT composite material as presented FIG. 3 (c and d), the survey scans of the specimen showed existence of Si, Al, and C elemental peaks arising from the valence energy levels for the respective atoms. The peak at about 74.4 eV in the high-resolution Al2p spectrum as shown in FIG. 3d confirmed the presence of Al—N and some Al—O bonds in the composite material. This unambiguously attests the successful introduction of Al into the final ceramic material. The binding energy of the C1s photoelectrons at ~284.5 eV suggest –sp$^2$ carbon peak. Further, X-ray diffraction (XRD) spectrum of SiAlCN in FIG. 3e substantiated that the material was indeed amorphous which is a typical of PDCs glass-ceramics. The Raman spectrum of the prepared SiAlCN/CNT composite, FIG. 3f, displayed characteristic D (~1350 cm$^{-1}$) and G (~1600 cm$^{-1}$) band, further corroborating the presence of CNTs in the pyrolyzed composite.

Further analysis of the hybrid composite involved thermogravimetric analysis (TGA), presented in FIG. 3g, and highlighted the extreme thermal stability of SiAlCN ceramic at 1000° C. flowing air, with negligible weight change. While the TGA spectrum of SiAlCN/CNT had a linear relationship between residual mass and oxidation temperature, which was observed to be 750±10° C. After the weight loss at about 750° C., the composite specimen showed stability in their weight. The TGA residual weight was 79% for SiAlCN/CNT specimen. The TGA data for 'neat' CNTs on the other hand indicated a 98% weight loss at ~510° C. Thus it can be concluded that the composite structure prepared by functionalization of nanotubes with SiAlCN ceramic improved oxidation resistance of CNTs by approx. 150° C. The weight loss at 750° C. is attributed to the combustion of CNTs in the composite, which suggests that the composite had approx. 30% CNTs by weight (about 25% more than the initial CNT loading in the Al-polymeric precursor).

Figure 4:
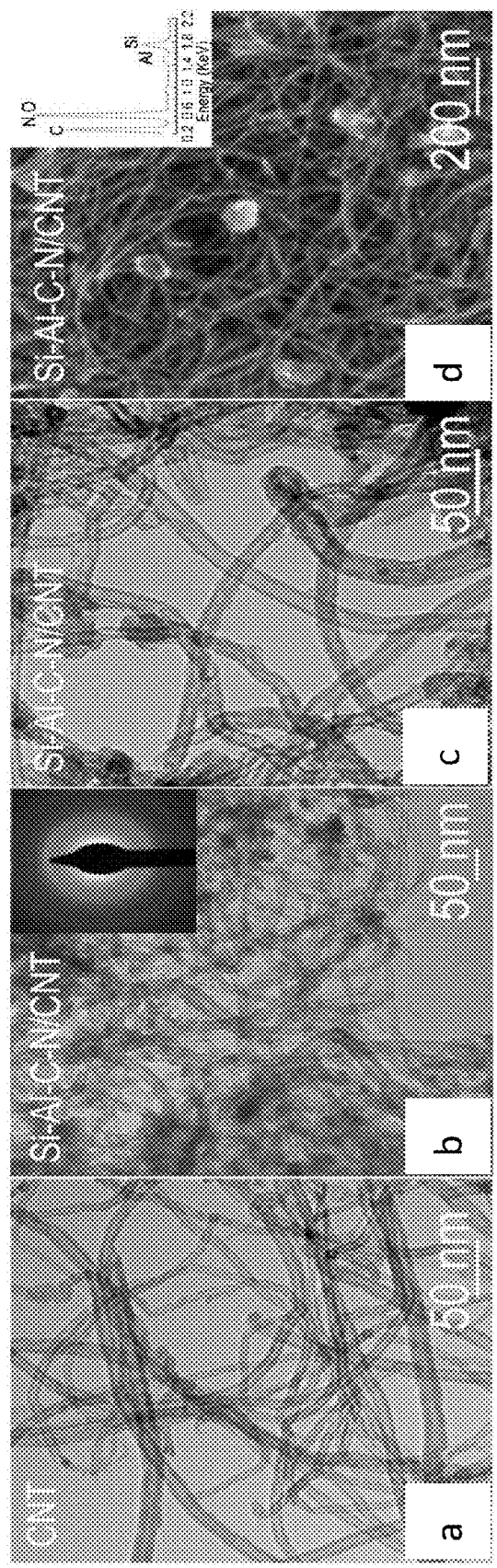
FIG. 4 shows (a) a TEM image of 'bare' CNT, (b) a TEM image of low magnification Si—Al—C—N/CNT (insert: SAED pattern), (c) a TEM image of high magnification SiAlCN/CNT; and (d) an SEM image of the spray coated SiAlCN/CNT electrode on copper current collector foil (insert: EDS spectrum)
Figure 5:
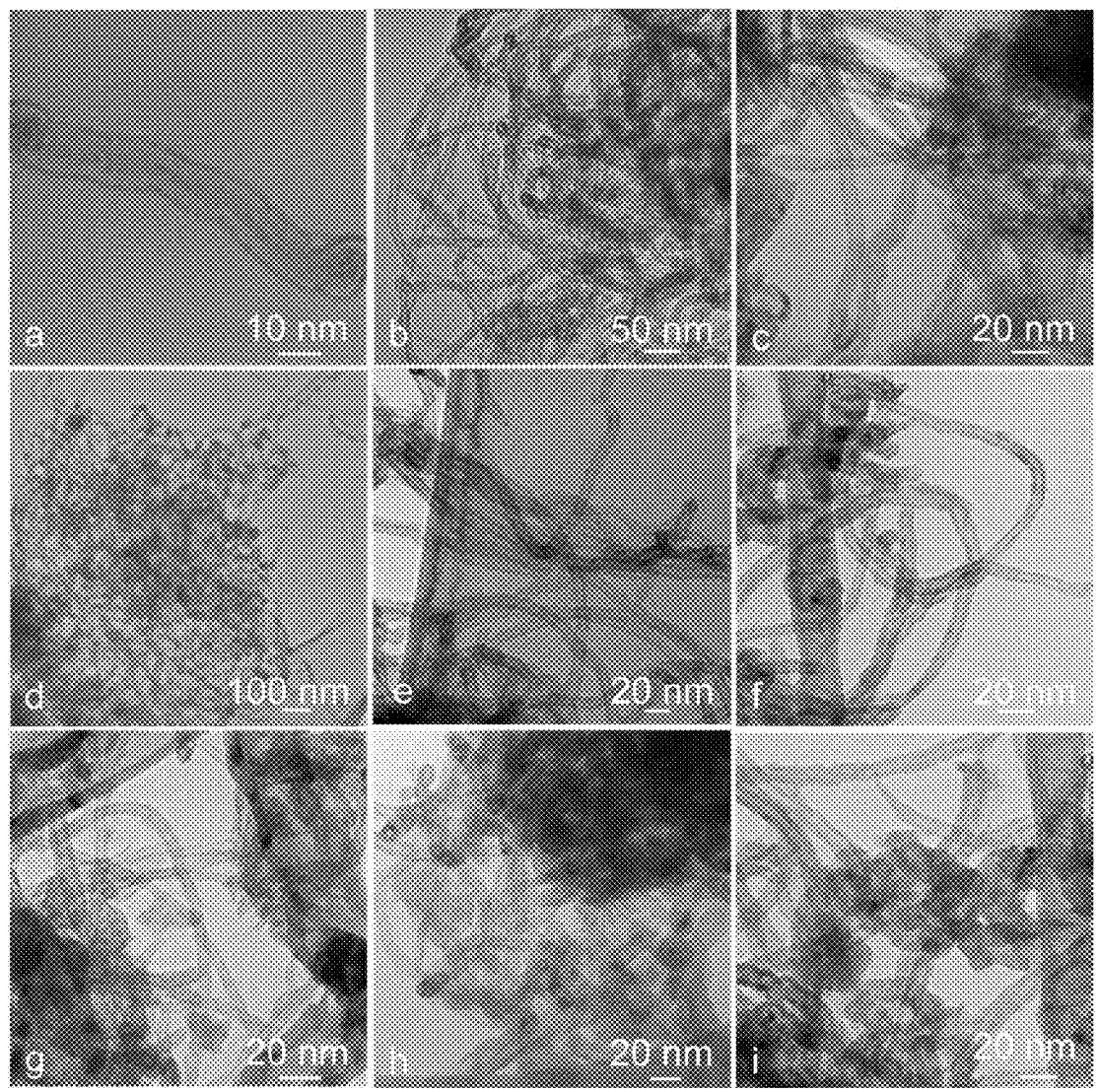
FIG. 5 shows various TEM images of as-prepared Si—Al—C—N/CNT composites.

Transmission electron microscope (TEM) images in FIG. 4 represent CNTs before and after functionalization by SiAlCN ceramic, respectively. Formation of composite nanowire-like structure consisting of nanometer thick ceramic shell on CNT core is confirmed. Some of the nanotubes were defective, some partially coated, and some were clumped in the form of particles as seen in FIG. 5. The TEM diffraction pattern for the composite was completely featureless thus confirming the amorphous nature of SiAlCN. FIG. 4 is the SEM image of the spray-coated specimen, which suggests that the coating was largely uniform and evenly covered the copper foil. The EDS spectrum in the insert is from the corresponding SEM image suggesting the presence of C, N, O, Al, and Si elements.

Electrochemical Cycling Results

Figure 6:
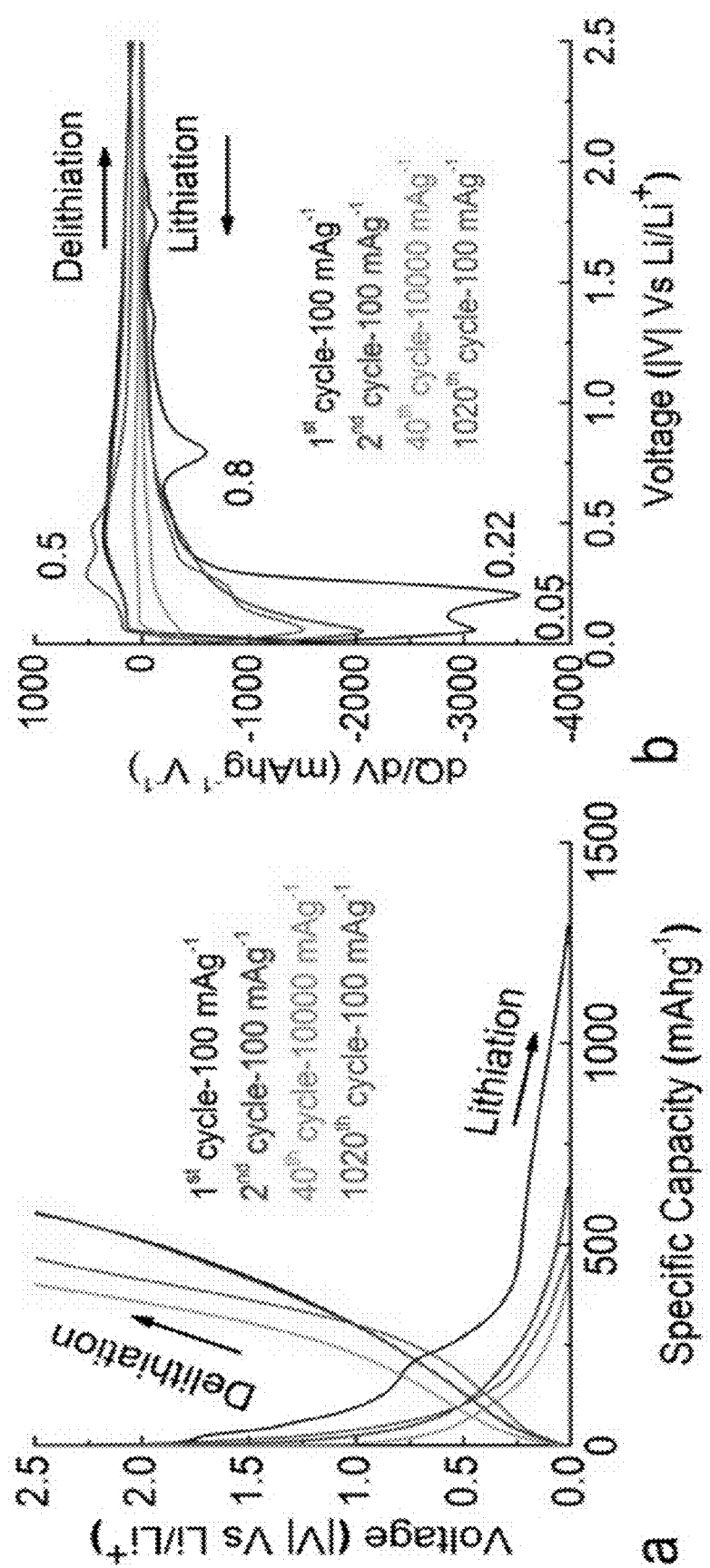
FIG. 6 shows graphs of electrochemical data. 1st, 2nd, 40th and 1020th cycle (a) voltage profile and (b) differential capacity curve for SiAlCN/CNT nanocomposite electrode.
Figure 7:
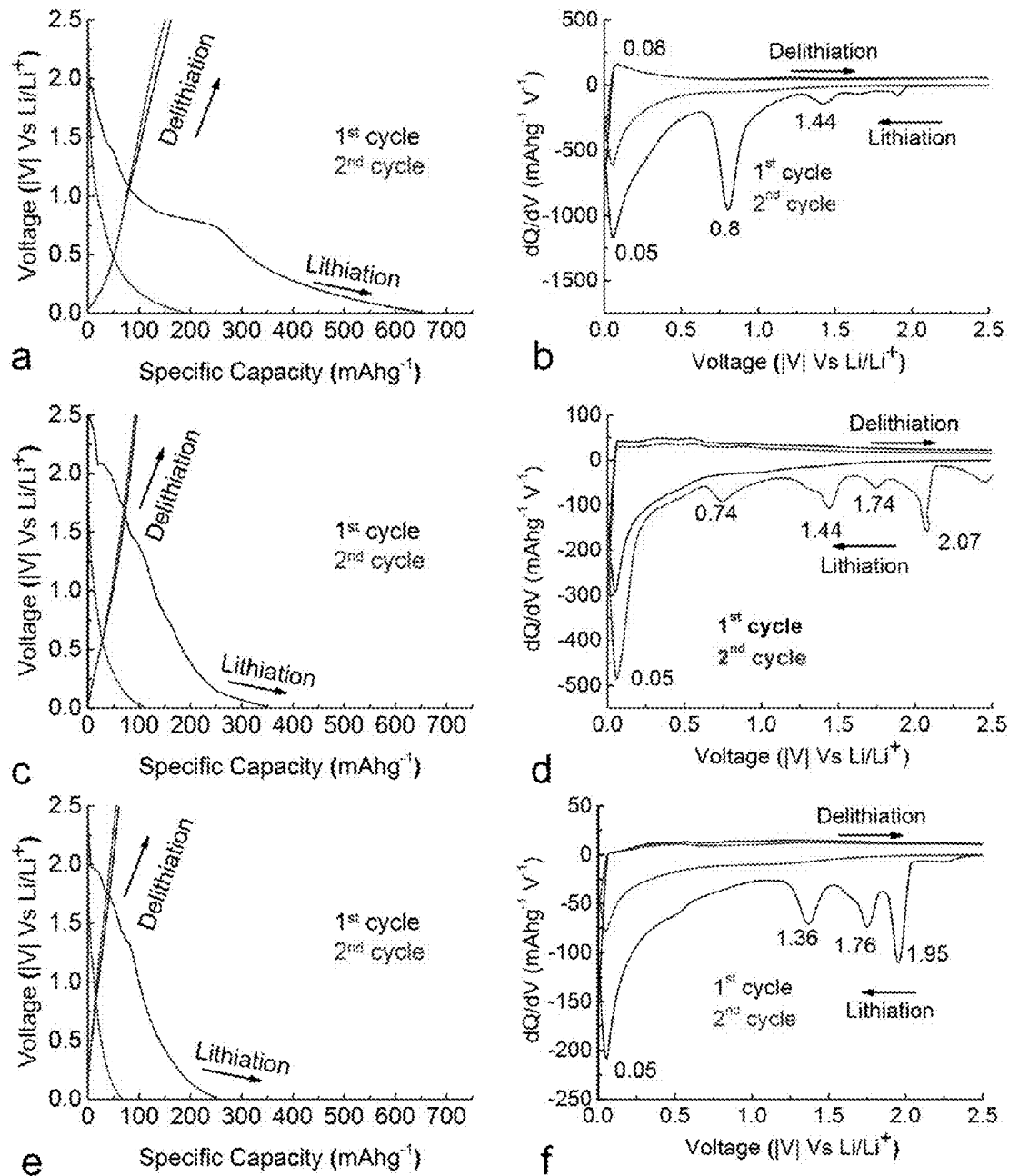
FIG. 7 shows graphs of first and second cycle voltage profile and differential capacity curves of (a, b) CNT, (c, d) SiAlCN and (e, f) SiCN spray coated electrodes.

Electrochemical behavior of the synthesized hybrid ceramic was studied by cycling it in a half-cell configuration against pure lithium metal. FIGS. 6a and 6b shows the charge/discharge profile and differential capacity curves of first two cycles for the hybrid composite electrode. First cycle discharge and charge capacity were observed to be 1294 and 577 mAh g$^{-1}$. This suggests that large percentage of Li is still consumed during SEI formation; however, this initial loss of Li maybe lowered by pre-lithiation in future studies. Further, the differential capacity curve showed reduction peaks typical to PDCs at 50, 220 and 800 mV and oxidation peak at 500 mV. The charge/discharge profile and differential capacity curves of spray coated 'neat' CNTs, SiAlCN, and SiCN ceramic (without binder or conducting agents) are compared in FIG. 7.

Even though the first cycle discharge capacity of CNTs was relatively high at ~670 mAh g$^{-1}$, it suffered from a large first cycle loss showing charge capacity of ~200 mAh g$^{-1}$. In case of the ceramic particle anodes the electrochemical performance was extremely low relative to the hybrid composite anode. The spray coated Si—C—N electrode performed poorly (first cycle charge capacity of 50 mAhg$^{-1}$ at 100 mAg$^{-1}$) and its cycling was stopped after first two cycles. Both the neat CNTs and SiAlCN ceramic electrodes' differential capacity curves had a major reduction peak at 0.05 V which is attributed to Li ion intercalation and another peak at 0.8 V which is attributed to SEI formation as this peak disappeared during the second cycle. In case of SiAlCN there were additional peaks centered at 1.44, 1.74, and 2.07 V.

On further cycling (FIG. 8), SiAlCN/CNT maintained its high capacity at ~564 mAh g$^{-1}$ (with 98% of the initial capacity retained) which is relatively high when compared to 'neat' CNTs and SiAlCN with charge capacities of ~140 and ~88 mAh g$^{-1}$, respectively after 5 cycles at 0.1 A g$^{-1}$. Later, the current density was gradually increased to 0.2, 0.4, 0.8, 1.6, 3.2, 6.4 and 10 A g$^{-1}$ for each 5 cycles consecutively. Impressively, the SiAlCN/CNT hybrid composite showed reversible capacity of 400 mAh g$^{-1}$ even at 10 A g$^{-1}$ which is approx. 70% of the first cycle charge capacity. When the cells were cycled back at 0.1 A g$^{-1}$, all the cells regained their initial charge capacities at 540, 130 and 77 mAh g$^{-1}$ for SiAlCN/CNT, CNTs, and SiAlCN, respectively. A similar trend was observed in areal charge capacity data, which is presented in FIG. 9.

Figure 8:
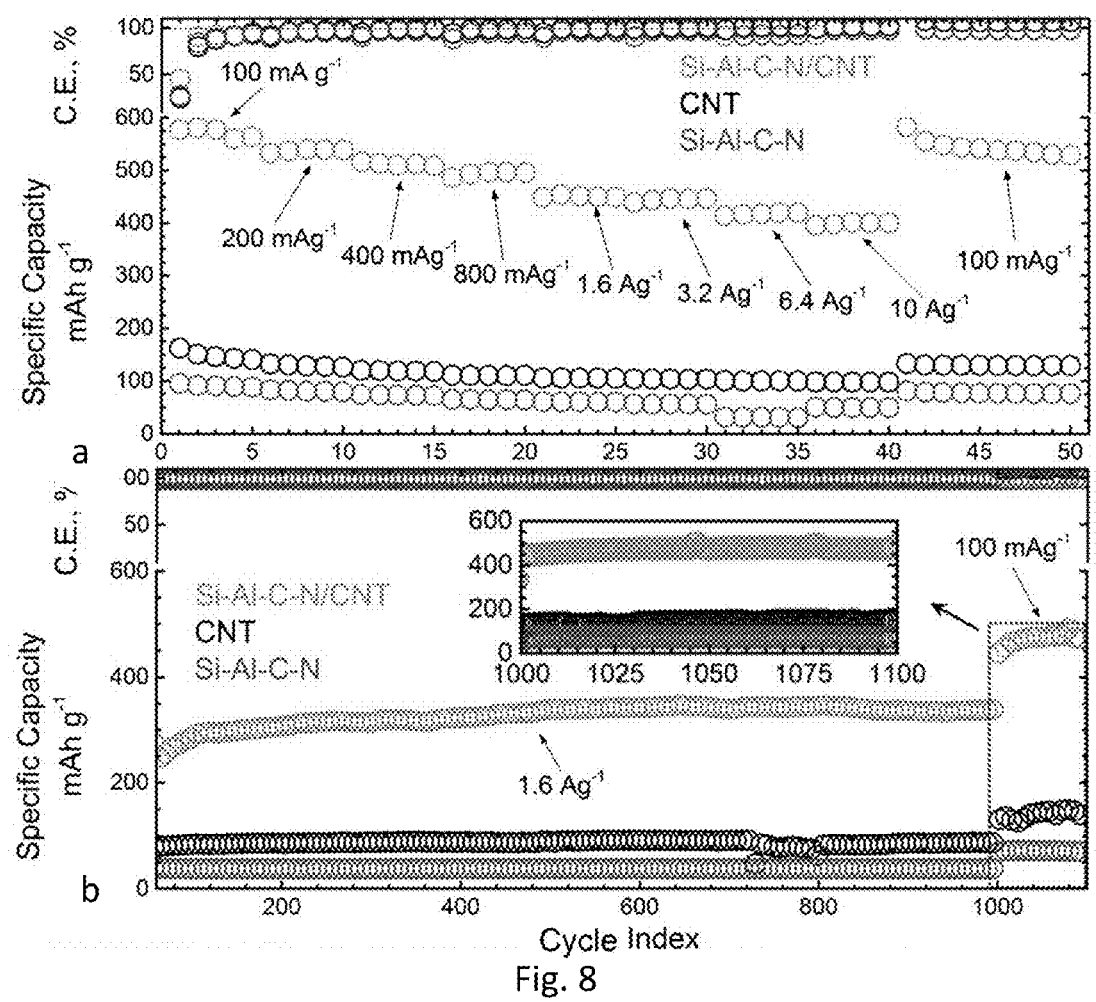
FIG. 8 shows graphs of charge capacity comparison of all electrodes: (a) asymmetrically cycled at different rates for every 5 cycles and (b) consecutively cycled symmetrically at 1600 mA g$^{-1}$ for 1000 cycles. Columbic efficiency is plotted for all the material on the upper portion of the respective graph. The detailed view in the insert shows the extreme stability of SiAlCN/CNT after 1000 cycles. All capacities are based on the total mass of the coated material.
Figure 9:
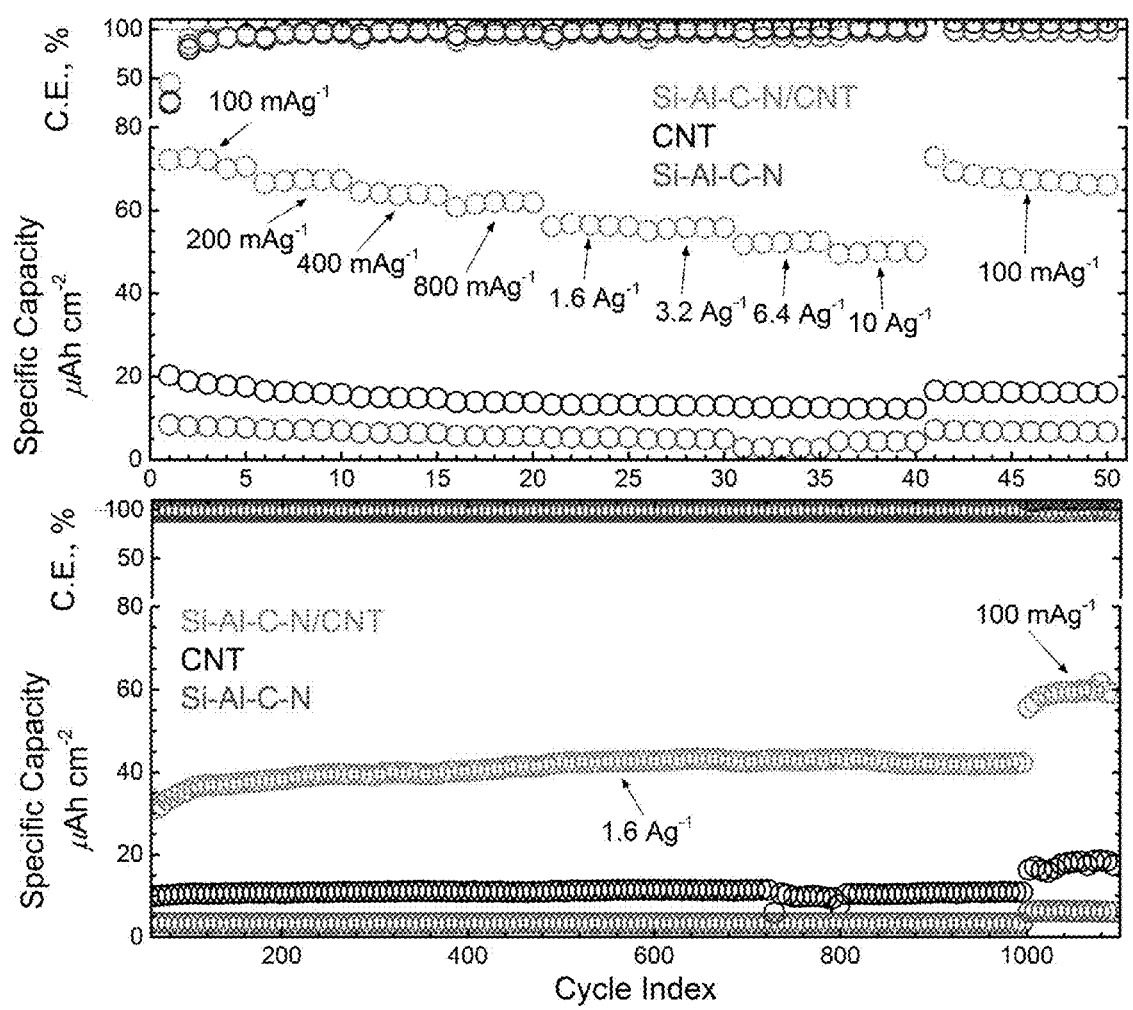
FIG. 9 shows graphs of the Areal charge capacity of all the anodes (top) asymmetrically cycled at different rates for every 5 cycles and (bottom) consecutively cycled symmetrically at 1600 mA g$^{-1}$ for 1000 cycles along with their cyclic efficiencies.

Long-term cycling behavior was studied by cycling symmetrically at 1.6 A g$^{-1}$ for approx. 1000 cycles (FIG. 8). SiAlCN/CNT had an impressively stable and high charge capacity of ~342 mAh·g$^{-1}$ (60% capacity retention) than CNTs and SiAlCN anode at ~91 and 37 mAh g$^{-1}$, respectively. All the cells regained most of their initial capacity when they were cycled back to the lower current density of 0.1 A g$^{-1}$ after 1000 cycles. SiAlCN/CNT was the best performing anode with 468 mAh g$^{-1}$ (81% retention w.r.t. first cycle) at 0.1 A g$^{-1}$ after 1000 cycles at 1.6 A g$^{-1}$ during both discharge and charge half cycles. The SiAlCN/CNT electrode represents considerable improvement over other polysilazane derived siliconcarbonitride ceramic and composite electrodes (with carbon nanotube and graphene prepared through slurry coating) reported in the literature. A comparison of first cycle charge capacity with other precursor-derived glass-ceramic electrodes is presented in Table 1.

is close to the measured conductivity of neat MWCNTs of approx. 4.22 S cm$^{-1}$, there-by making the composite conducting enough to eliminate conductive agents during electrode preparation.

Figure 10:
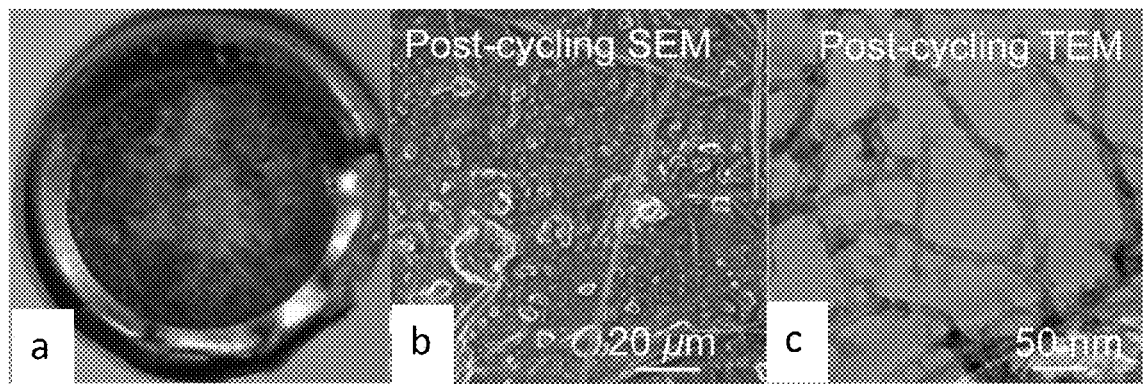
FIG. 10 shows images of (a) optical, (b) SEM images, and (c) high resolution TEM image of dissembled SiAlCN/CNT electrode after 1100 cycles. Glass separator residue can be seen as white cotton like material on the surface of electrode in (a). The cell was dissembled in the lithiated state.
Figure 11:
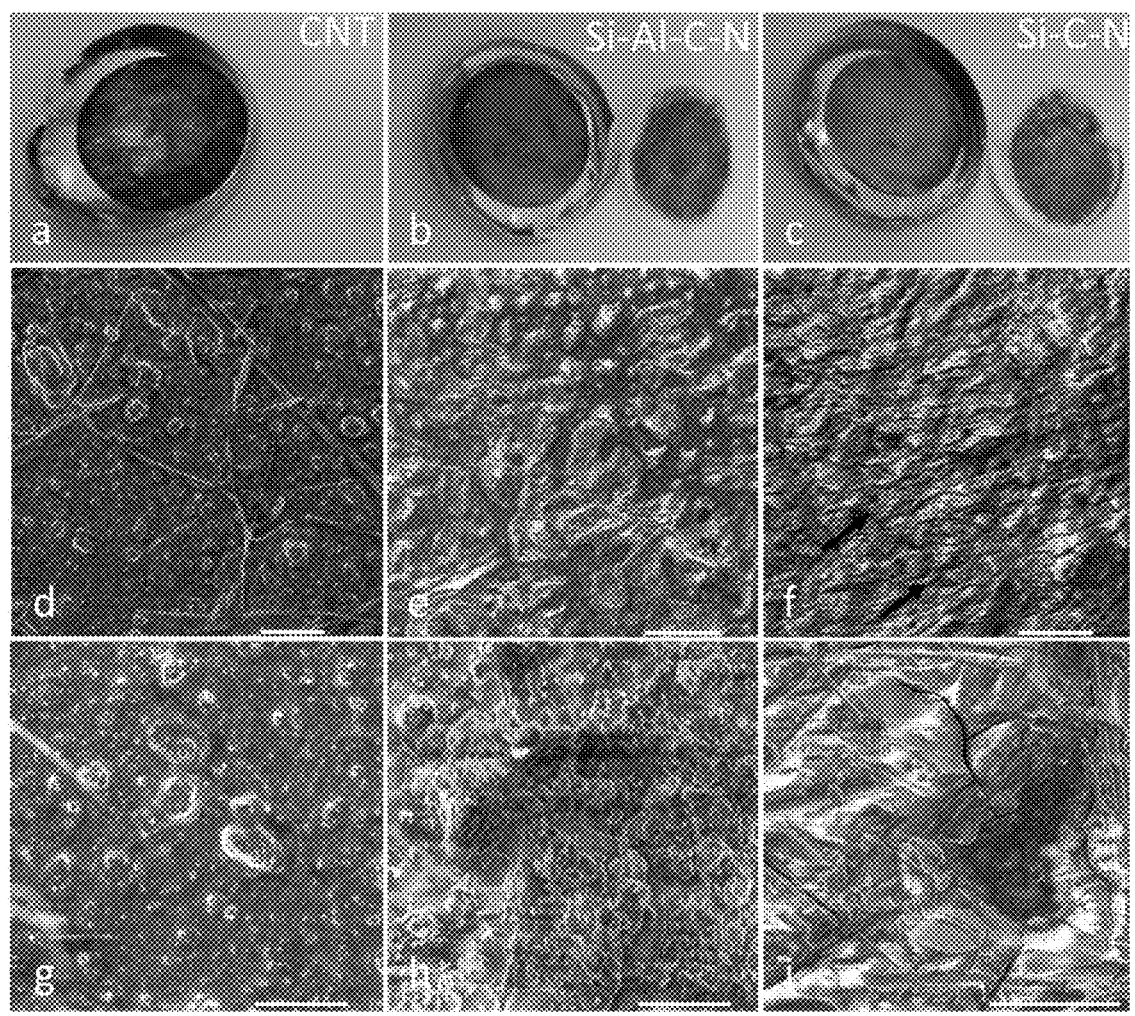
FIG. 11 shows images (a through c) Post cycling digital camera photographs of CNT, SiAlCN and SiCN cycled electrodes, respectively. Most SiAlCN and SiCN material was stuck to the glass separator (shown next to the electrodes) due to poor adhesion. (d through e) and (g through i) are the corresponding high and low magnification SEM images. Scale bar is 40 micrometers for (d through f) and 10 micrometers for (g through i)

Later, the cells were disassembled in their lithiated state to study the effect of long-term cycling on their morphology and chemical structure. FIG. 10 shows the optical photograph, high-resolution SEM image, and TEM image of SiAlCN/CNT electrode after 1100 cycles, respectively. SEM and optical images of all other cycled electrodes are presented in FIG. 11 Remarkably, SiAlCN/CNT and CNTs specimens looked intact with no large or micro surface cracks. Further, stable SEI layer formation and the presence of glass fiber separator could be observed (FIG. 10). However, in the case of SiAlCN and Si—C—N particle electrodes, delamination of material from the copper current collector was clearly evident. This was hardly surprising considering the dispersions made with SiAlCN or Si—C—N particles were relatively unstable and the adhesion of the spray-coated particles to the current collector foil was

TABLE 1

Summary of the experimental results compared with various precursor-derived Si—C—N glass-ceramic and composite electrodes for LIB

| Material | 1$^{st}$ Cycle Charge, mAh g$^{-1}$ | Binder and Conductive Agents | Capacity at Max. Current Density Tested, mAh g$^{-1}$ | Max. Number of Cycles Tested |
|---|---|---|---|---|
| Si—Al—C—N/CNT (present work) | 577 | No | 400 (10000 mA g$^{-1}$) | 1100 |
| MWCNT (present work) | 162 | No | 98 (10000) | 1100 |
| Si—Al—C—N (present work) | 96 | No | 50 (10000) | 1100 |
| SiCN-1100° C.$^A$ | 263 | Yes | 100 (36) | 50 |
| SiCN-1300° C./O$_2$$^A$ | 291 | Yes | 250 (72) | 60 |
| SiCN-1100° C.$^B$ | 254 | Yes | 95 (360) | 10 |
| SiCN-1000° C.$^C$ | 456 | Yes | 171 (100) | 30 |
| SiCN-Graphite$^D$ | 312 | Yes | 200 (720) | 275 |
| SiCN-Graphene$^E$ | 420 | Yes | 440 (40) | 50 |
| Si(B)CN—CNT$^F$ | 362 | Yes | 430 (100) | 30 |

$^A$Graczyk-Zajac, M.; Mera, G.; Kaspar, J.; Riedel, R., Electrochemical Studies of Carbon-Rich Polymer-Derived SiCN Ceramics as Anode Materials for Lithium-Ion Batteries. J. Euro. Ceram. Soc. 2010, 30, 3235.
$^B$Kaspar, J.; Mera, G.; Nowak, A. P.; Graczyk-Zajac, M.; Riedel, R., Electrochemical Study of Lithium Insertion into Carbon-Rich Polymer-Derived Silicon Carbonitride Ceramics. Electrochim. Acta 2010, 56, 174.
$^C$Su, D.; Li, Y. L.; Feng, Y.; Jin, J., Electrochemical Properties of Polymer-Derived SiCN Materials as the Anode in Lithium Ion Batteries. J. Am. Ceram. Soc. 2009, 92, 2962.
$^D$Graczyk-Zajac, M.; Fasel, C.; Riedel, R. Polymer-derived-SiCN Ceramic/Graphite Composite as Anode Material with Enhanced Rate Capability for Lithium Ion Batteries. J. Power Sources 2011, 196, 6412.
$^E$Kolb, R.; Fasel, C.; Liebau-Kunzmann, V.; Riedel, R., SiCN/C-Ceramic Composite as Anode Material for Lithium Ion Batteries. J. Euro. Ceram. Soc. 2006, 26, 3903.
$^F$Bhandavat, R.; Singh, G. Improved Electrochemical Capacity of Precursor-Derived Si(B)CN-Carbon Nanotube Composite as Li-Ion Battery Anode. ACS Appl. Mater. Interfaces 2012, 4, 5092.

Figure 12:
FIG. 12 shows an image comparing SiAlCN and SiAlCN/CNT dispersions in Toluene/NMP after they were kept stable for 6 hours.

The improvement in electrochemical performance of SiAlCN/CNT electrode can be attributed to following synergistic effects: 1) 3-dimensional nature of the PDC electrode due to interfacing with CNTs and increase in surface area, making the electrode more ion-accessible while still maintaining an integral electrical and mechanical contact with the ceramic shell throughout the electrode and the copper current collector foil, respectively and, 2) the robust nanodomain structure and improved electrical conductivity due to Al-doping of Si—C—N that improved the ceramic's Li-cycleability and simultaneously provided protection to high current carrying CNTs against exfoliation at extreme C-rates. The electrical conductivity of SiAlCN ceramic (measured using four-point technique) was approx. 1.2×10$^{-4}$ S cm$^{-1}$ which is many folds higher than polysilazane-derived Si—C—N with a reported conductivity of approx. 10$^{-7}$ S cm$^{-1}$. With CNTs embedded in the matrix, the conductivity further increased to approx. 0.2 S cm$^{-1}$ which generally poor FIG. 12. On closer examination using SEM, some micro cracks were observed on the surface of the cycled electrode and the charge capacity degradation as observed in the long-term cycling data could be attributed to these cracks. TEM image of the cycled SiAlCN/CNT electrodes indicated volume expansion and SEI formation on the surface of nanotubes. However, when compared to the composite material before cycling, the overall composite nanostructure still looked largely intact with complete CNT core structure and unbroken SiAlCN coating being retained.

CONCLUSIONS

In summary, we synthesized SiAlCN/CNT shell/core composite by controlled thermal conversion of Al-modified polysilazane single-source precursor on the surfaces of carbon nanotubes and studied its electrochemical performance as Li-ion battery electrode for the first time. SEM and TEM images proved its morphology to be core-shell, while XPS, FTIR, NMR and XRD analysis revealed the chemical structure of the pyrolyzed glass-ceramic shell. TGA was utilized to highlight the incredible thermal stability of the composite in flowing air up to 750° C. Dispersions in NMP/Toluene at approx. 8 mg·cm$^{-2}$ were then directly spray-coated on Cu current collector foil as a fast method of electrode preparation. SiAlCN/CNTs had an impressive charge capacity of 400 mAh g$^{-1}$ even at 10,000 mA g$^{-1}$ which was 70% of its initial reversible capacity. Long term symmetrical cycling for 1000 cycles at 1600 mA g$^{-1}$ showed an equally impressive stable charge capacity of ~342 mAh g$^{-1}$ with near 100% efficiency. Lastly, post-cycling SEM analysis of the cycled electrode showed that the coating was largely intact with no major mechanical damage, highlighting the robust nature of the PDC composites.

Example 2

In this Example, the laser irradiance behavior and resulting structural evolution of SiAlCN/CNTs composite coatings was examined. A SiAlCN/CNTs composite composition was prepared and spray-coated onto copper substrates. The spraying was done with longitudinal passes while the substrate surface temperature was raised to 80° C. using a hot plate. Frequent stops between the passes allowed the solvent to evaporate and thereby form a uniform compact coating. Spray coating was carried out until the appropriate dark black coating thickness was visually realized with an approximate thickness of 10 µm. The coated copper test specimens were then maintained at 100° C. on a hot plate for 12 hours to ensure removal of volatile entities. The substrate was a circular copper disc (weighing about 20 grams) with about 26 mm diameter and about 13 mm thickness.

Figure 13:
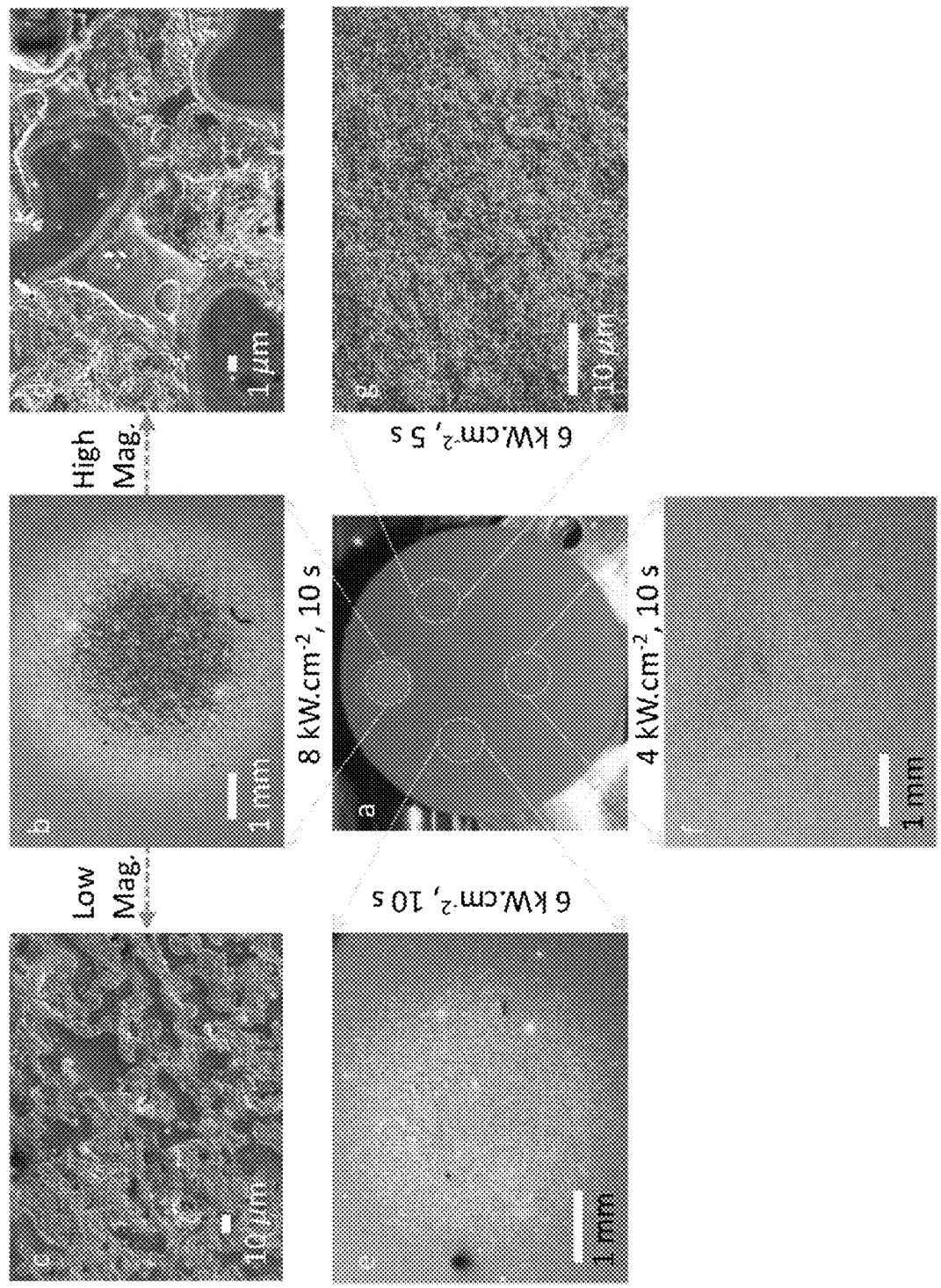
FIG. 13 shows imaging of a laser-irradiated copper disc from Example 2: (a) Digital camera; (b through g) SEM images.

The coated discs were exposed to laser irradiation at increasing dosages using 1 micrometer laser wavelength at 10 kW average power for 10 seconds. The exposed and unexposed areas of the coatings were analyzed and compared using electron microscopy (EM) and digital imagery. The results are shown in FIG. 13. From the digital camera image of copper disc spray coated with SiAlCN/CNT composite material, four laser-irradiated spots are visible. The SEM images of the irradiated spots were taken at various powder densities and irradiation times. It can be seen that the coating was largely intact even upon irradiation at 8 kW/cm$^2$ for 10 seconds, although the copper substrate melted causing island-like formation in the coating (see-Image d). No damage was observed for 6 and 4 kW/cm$^2$ irradiation.

We claim:

1. A ceramic nanocomposite comprising:
   a plurality of carbon nanotubes having respective sidewalls; and
   a layer of a polymer-derived ceramic adjacent said sidewalls, said polymer-derived ceramic being bonded to said sidewalls forming a protective shell thereon, wherein said polymer-derived ceramic is formed from an aluminum-modified silazane that is a room temperature liquid-phase polymer.

2. The ceramic nanocomposite of claim 1, wherein said carbon nanotubes chemically interface with said aluminum-modified silazane.

3. The ceramic nanocomposite of claim 1, wherein said silazane is poly(ureamethylvinyl)silazane.

4. The ceramic nanocomposite of claim 1, wherein said ceramic nanocomposite is resistant to oxidation in flowing air at a temperature of up to about 1000° C.

5. The ceramic nanocomposite of claim 1, wherein said ceramic nanocomposite is selected from the group consisting of nanowires, nanorods, nanosheets, and combinations thereof.

6. The ceramic nanocomposite of claim 1, wherein said carbon nanotubes are selected from the group consisting of single-wall carbon nanotubes, double-wall carbon nanotubes, multi-wall carbon nanotubes, and mixtures thereof.

7. A structure comprising:
   a substrate having a surface; and
   a layer of the ceramic nanocomposite according to claim 1 adjacent said substrate surface.

8. The structure of claim 7, wherein said layer is resistant to:
   oxidation in flowing air at a temperature of up to about 1000° C.; or
   laser irradiation up to about 8 kWcm$^{-2}$ at a wavelength of about 1 µm at 10 kW average power, for about 10 seconds without burning, delamination, or deformation of said layer.

9. The structure of claim 7, wherein said substrate is selected from the group consisting of metallic surfaces, natural woven fibers, synthetic woven fibers, natural nonwoven fibers, synthetic nonwoven fibers, natural or synthetic mats, natural or synthetic cloth, and combinations thereof.

10. The structure of claim 7, wherein said substrate is an article of manufacture selected from the group consisting of high temperature sensors, turbine blades, engine parts, microelectronic components, solar cells, electrodes, protective coatings, tubing, wires, pump shafts, cylinders, spindles or sleeves, induction coils, and combinations thereof.

11. A method of forming the ceramic nanocomposite of claim 1, said method comprising:
   mixing the plurality of carbon nanotubes with the aluminum-modified silazane that is a room temperature liquid-phase polymer to yield respective sidewall-functionalized nanotubes comprising a layer of aluminum-modified silazane adjacent said nanotube sidewall;
   crosslinking said layer of aluminum-modified silazane to yield a pre-ceramic nanocomposite comprising a solid pre-ceramic layer adjacent the sidewall of the carbon nanotubes, wherein said pre-ceramic layer comprises a crosslinked network of aluminum-modified silicon-based compounds coating the sidewall of the nanotubes; and
   converting said pre-ceramic layer to ceramic to yield a ceramic nanocomposite comprising a layer of aluminum-modified polymer-derived ceramic coating the sidewall of the nanotubes.

12. The method of claim 11, wherein said carbon nanotubes are first dispersed in a solvent system prior to said mixing with said aluminum-modified silazane.

13. The method of claim 12, further comprising drying said sidewall-functionalized nanotubes to evaporate said solvent after said mixing.

14. The method of claim 11, wherein said pre-ceramic layer comprises aluminum crosslinkages linking said silicon-based compounds.

15. The method of claim 11, further comprising reducing said pre-ceramic nanocomposite into a free-flowing powder after said crosslinking prior to said converting.

16. The method of claim 15, wherein said reducing comprises grinding, milling, pulverizing, and/or crushing the pre-ceramic composition into said powder.

17. The method of claim 11, wherein said converting comprises pyrolyzing said crosslinked network of aluminum-modified silicon-based compounds.

18. The method of claim 11, wherein said ceramic nanocomposite is a free-flowing black powder.

19. The method of claim 11, wherein said aluminum-modified polymer-derived ceramic layer is characterized by aluminum substantially uniformly distributed throughout a polymer-derived ceramic network.

20. A method of forming a polymer-derived ceramic coating, said method comprising:
dispersing a ceramic nanocomposite powder in a solvent system to form a ceramic dispersion, said powder comprising discrete particulates, each of said particulates comprising the nanocomposite according to claim 1;
applying said ceramic dispersion to a substrate surface to form a layer thereon; and
heating said layer to evaporate said solvent system and yield a coated substrate having said ceramic nanocomposite coating adjacent said substrate surface.

21. The method of claim 20, wherein said substrate comprises a metal selected from the group consisting of copper and alloys thereof.

22. The method of claim 20, wherein said substrate has a planar surface.

23. The method of claim 20, wherein said substrate has an uneven surface.

24. A powdered composition comprising a plurality of free-flowing particulates, each of said particulates consisting of a ceramic nanocomposite according to claim 1.

25. The powdered composition of claim 24, being substantially free of any binders and/or conducting agents.

26. The powdered composition of claim 24, said powdered composition having a four-point electrical conductivity of at least 0.2 S/cm.

* * * * *